US010280240B2

(12) United States Patent
Hagadorn et al.

(10) Patent No.: US 10,280,240 B2
(45) Date of Patent: May 7, 2019

(54) METALLOCENE CATALYST COMPOSITIONS AND POLYMERIZATION PROCESS THEREWITH

(71) Applicant: ExxonMobil Chemical Patents Inc., Baytown, TX (US)

(72) Inventors: John R. Hagadorn, Houston, TX (US); Jian Yang, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/450,963

(22) Filed: Mar. 6, 2017

(65) Prior Publication Data

US 2017/0342175 A1 Nov. 30, 2017

Related U.S. Application Data

(63) Continuation-in-part of application No. PCT/US2016/034784, filed on May 27, 2016.

(51) Int. Cl.
| | | |
|---|---|---|
| *C07F 17/00* | (2006.01) | |
| *C08F 4/6592* | (2006.01) | |
| *C08F 10/00* | (2006.01) | |
| *C08F 110/06* | (2006.01) | |
| *B01J 31/16* | (2006.01) | |
| *C08F 4/00* | (2006.01) | |

(52) U.S. Cl.
CPC .......... *C08F 110/06* (2013.01); *B01J 31/16* (2013.01); *C07F 17/00* (2013.01); *C08F 4/00* (2013.01); *C08F 4/65925* (2013.01); *C08F 4/65927* (2013.01)

(58) Field of Classification Search
CPC .. C08F 4/65927; C08F 4/65908; C08F 10/06; C08F 4/65925; C07F 17/00
See application file for complete search history.

(56) References Cited

U.S. PATENT DOCUMENTS

| | | | |
|---|---|---|---|
| 5,049,535 A | 9/1991 | Resconi et al. | |
| 5,276,208 A | 1/1994 | Winter et al. | |
| 5,278,264 A | 1/1994 | Spaleck et al. | |
| 5,411,994 A | 5/1995 | Galli et al. | |
| 5,459,117 A | 10/1995 | Ewen | |
| 5,532,396 A | 7/1996 | Winter et al. | |
| 5,539,076 A | 7/1996 | Nowlin et al. | |
| 5,543,373 A | 8/1996 | Winter et al. | |
| 5,547,756 A | 8/1996 | Kamo et al. | |
| 5,585,509 A | 12/1996 | Langhauser et al. | |
| 5,589,549 A | 12/1996 | Govoni et al. | |
| 5,631,202 A | 5/1997 | Ewen | |
| 5,661,098 A | 8/1997 | Harrison et al. | |
| 5,696,045 A | 12/1997 | Winter et al. | |
| 5,700,886 A | 12/1997 | Winter et al. | |
| 5,770,753 A | 6/1998 | Kueber et al. | |
| 5,786,432 A | 7/1998 | Kueber et al. | |
| 5,840,644 A | 11/1998 | Kueber et al. | |
| 5,990,242 A | 11/1999 | Naga et al. | |
| 5,869,584 A | 12/1999 | Winter et al. | |
| 6,001,764 A | 12/1999 | Pullukat et al. | |
| 6,028,140 A | 2/2000 | Collina et al. | |
| 6,051,727 A | 4/2000 | Kueber et al. | |
| 6,069,213 A | 5/2000 | Nemzek et al. | |
| 6,121,182 A | 9/2000 | Okumura et al. | |
| 6,150,481 A | 11/2000 | Winter et al. | |
| 6,174,930 B1 | 1/2001 | Agarwal et al. | |
| 6,242,544 B1 | 6/2001 | Kueber et al. | |
| 6,255,506 B1 | 7/2001 | Kueber et al. | |
| 6,262,195 B1 | 7/2001 | Dall'Occo et al. | |
| 6,329,315 B1 | 12/2001 | Denton et al. | |
| 6,350,830 B1 | 2/2002 | Gores et al. | |
| 6,376,627 B1 | 4/2002 | Burkhardt et al. | |
| 6,399,533 B2 | 6/2002 | Sacchetti et al. | |
| 6,429,250 B1 | 8/2002 | Rohrmann et al. | |
| 6,444,833 B1 | 9/2002 | Ewen et al. | |
| 6,492,465 B1 | 12/2002 | Burkhardt et al. | |
| 6,559,252 B1 | 5/2003 | Horton et al. | |
| 6,608,224 B2 | 8/2003 | Resconi et al. | |
| 6,635,779 B1 | 10/2003 | Ewen et al. | |
| 6,673,736 B2 | 1/2004 | Kellum et al. | |
| 6,777,366 B2 | 8/2004 | Gauthier et al. | |
| 6,777,367 B2 | 8/2004 | Gauthier et al. | |
| 6,787,616 B2 | 9/2004 | Takemori et al. | |
| 6,841,501 B2 | 1/2005 | Resconi et al. | |
| 6,846,943 B2 | 1/2005 | Nakano et al. | |
| 6,855,783 B2 | 2/2005 | Gauthier et al. | |
| 6,870,016 B1 | 3/2005 | Burkhardt et al. | |
| 6,878,786 B2 | 4/2005 | Resconi et al. | |

(Continued)

FOREIGN PATENT DOCUMENTS

| | | |
|---|---|---|
| CN | 102731691 | 2/2014 |
| EP | 0576970 | 1/1994 |

(Continued)

OTHER PUBLICATIONS

Resconi et al., "Metallocene Catalysts for Propylene Polymerization," Polypropylene Handbook, Pasquini, Ed., Chapter 2.2, Hanser Publications, Munic, 2005.
U.S. Appl. No. 14/324,427, filed Jul. 7, 2014.
U.S. Appl. No. 15/000,731, filed Jan. 19, 2016.
Schmidt et al., "Synthesis and characterization of unbridged metallocene dichloride complexes with two differently mono-substituted indenyl ligands and their application as catalysts for the polymerization of ethane and propene," Journal of Molecular Catalysis A: Chemical, 2001, 172 (1-2), pp. 43-65.
U.S. Appl. No. 14/572,195, filed Dec. 16, 2014.
U.S. Appl. No. 14/324,408, filed Jul. 7, 2014.
U.S. Appl. No. 14/324,333, filed Jul. 7, 2014.

(Continued)

*Primary Examiner* — Caixia Lu

(57) ABSTRACT

This invention relates homogeneous (solution) polymerization of propylene at higher temperatures (80° C. or more) using bisindenyl metallocene catalyst compounds having long (at least 4 carbon atoms) linear alkyl groups substituted at the 2-position and substituted or unsubstituted aryl groups at the 4-position.

36 Claims, 4 Drawing Sheets

(56) References Cited

U.S. PATENT DOCUMENTS

| | | |
|---|---|---|
| 6,916,886 B2 | 7/2005 | Morioka et al. |
| 6,949,614 B1 | 9/2005 | Schottek et al. |
| 6,953,829 B2 | 10/2005 | Kratzer et al. |
| 6,992,153 B1 | 1/2006 | Collina et al. |
| 7,034,173 B2 | 4/2006 | Schottek |
| 7,122,498 B2 | 10/2006 | Hart et al. |
| 7,141,527 B1 | 11/2006 | Van Baar et al. |
| 7,314,903 B2 | 1/2008 | Resconi et al. |
| 7,342,078 B2 | 3/2008 | Schottek et al. |
| 7,405,261 B2 | 7/2008 | Schulte et al. |
| 7,452,949 B2 | 11/2008 | Okumura et al. |
| 7,569,651 B2 | 8/2009 | Schottek et al. |
| 7,615,597 B2 | 11/2009 | Resconi et al. |
| 7,799,880 B2 | 9/2010 | Ciaccia |
| 7,829,495 B2 | 11/2010 | Floyd et al. |
| 7,964,679 B2 | 6/2011 | Resconi et al. |
| 7,985,799 B2 | 7/2011 | Resconi et al. |
| 8,222,356 B2 | 7/2012 | Kipke et al. |
| 8,299,287 B2 | 10/2012 | Dimeska et al. |
| 8,318,872 B2 | 11/2012 | Savatsky et al. |
| 8,399,375 B2 | 3/2013 | Itan et al. |
| 8,415,492 B2 | 4/2013 | Sell et al. |
| 8,507,706 B2 | 8/2013 | Dimeska et al. |
| 8,557,917 B2 | 10/2013 | Leskinen et al. |
| 8,729,206 B2 | 5/2014 | Resconi et al. |
| 9,193,856 B2 | 11/2015 | Ebata et al. |
| 9,249,239 B2 | 2/2016 | Jian et al. |
| 9,376,559 B2 | 6/2016 | Holtcamp et al. |
| 9,458,257 B2 | 10/2016 | Funaya et al. |
| 9,464,145 B2 | 10/2016 | Yang et al. |
| 9,644,047 B2 | 5/2017 | Yang et al. |
| 9,718,900 B2 | 8/2017 | Giesbrecht |
| 9,725,537 B2 | 8/2017 | Luo et al. |
| 9,725,569 B2 | 8/2017 | Holtcamp et al. |
| 9,738,779 B2 | 8/2017 | Luo et al. |
| 9,745,390 B2 | 8/2017 | Yang et al. |
| 9,809,664 B2 | 11/2017 | Luo et al. |
| 9,834,628 B2 | 12/2017 | Canich et al. |
| 9,920,176 B2 | 3/2018 | Luo et al. |
| 9,944,665 B2 | 4/2018 | Yang et al. |
| 10,077,325 B2 | 9/2018 | Luo et al. |
| 10,119,016 B2 | 11/2018 | Luo et al. |
| 2001/0053833 A1 | 12/2001 | Nakano et al. |
| 2002/0147105 A1 | 10/2002 | Shamshoum et al. |
| 2003/0171207 A1 | 9/2003 | Shih et al. |
| 2003/0236365 A1 | 12/2003 | Tian et al. |
| 2004/0204310 A1 | 10/2004 | Gauthier et al. |
| 2005/0003951 A1 | 1/2005 | Ferraro et al. |
| 2005/0085376 A1 | 4/2005 | Nagy et al. |
| 2005/0182266 A1 | 8/2005 | Schulte et al. |
| 2007/0004814 A1 | 1/2007 | Resconi et al. |
| 2007/0055021 A1 | 3/2007 | Chandrashekar et al. |
| 2007/0179051 A1 | 8/2007 | Mihan et al. |
| 2009/0018267 A1 | 1/2009 | Vestberg et al. |
| 2009/0062492 A1 | 3/2009 | Luo et al. |
| 2009/0259007 A1 | 10/2009 | Ciaccia |
| 2010/0267907 A1 | 10/2010 | Dimeska et al. |
| 2011/0034649 A1 | 2/2011 | Standaert et al. |
| 2011/0081817 A1 | 4/2011 | Bieser et al. |
| 2011/0112262 A1 | 5/2011 | Gauthier et al. |
| 2011/0160373 A1 | 6/2011 | Bernreitner et al. |
| 2011/0230630 A1 | 9/2011 | Sell et al. |
| 2013/0253124 A1 | 9/2013 | Bernreiter et al. |
| 2013/0345376 A1 | 12/2013 | Luo et al. |
| 2014/0221514 A1 | 8/2014 | Datta et al. |
| 2014/0303308 A1 | 10/2014 | Grestenberger et al. |
| 2014/0357771 A1 | 12/2014 | Tranninger et al. |
| 2015/0025205 A1 | 1/2015 | Jian et al. |
| 2015/0025208 A1 | 1/2015 | Yang et al. |
| 2015/0119537 A1 | 4/2015 | Holtcamp et al. |
| 2015/0183893 A1 | 7/2015 | Yang et al. |
| 2016/0032025 A1 | 2/2016 | Giesbrecht |
| 2016/0137763 A1 | 5/2016 | Holtcamp et al. |
| 2016/0244539 A1 | 8/2016 | Resconi et al. |
| 2016/0335619 A1 | 12/2016 | Ye et al. |
| 2016/0355618 A1 | 12/2016 | Luo et al. |
| 2016/0355656 A1 | 12/2016 | Luo et al. |
| 2017/0253656 A1 | 9/2017 | Penta et al. |
| 2017/0342175 A1 | 11/2017 | Hagadorn et al. |
| 2018/0142045 A1 | 5/2018 | Luo |
| 2018/0142046 A1 | 5/2018 | Luo |
| 2018/0162964 A1 | 6/2018 | Yang et al. |
| 2018/0179309 A1 | 6/2018 | Luo et al. |

FOREIGN PATENT DOCUMENTS

| | | |
|---|---|---|
| EP | 0834519 | 4/1998 |
| EP | 1205493 | 5/2002 |
| EP | 1380598 | 1/2004 |
| EP | 1541598 | 6/2005 |
| JP | 2003-073414 | 3/2003 |
| JP | 2012-214709 | 11/2012 |
| WO | 01/058970 | 8/2001 |
| WO | 02/002575 | 1/2002 |
| WO | 02/002576 | 1/2002 |
| WO | WO0148034 | 10/2002 |
| WO | 03/002583 | 1/2003 |
| WO | 03/045551 | 6/2003 |
| WO | 03/051934 | 6/2003 |
| WO | 2004/052945 | 6/2004 |
| WO | 2004/092225 | 10/2004 |
| WO | 2004/106351 | 12/2004 |
| WO | 2014/016318 | 1/2014 |
| WO | 2015/065676 | 5/2015 |
| WO | 2015/070360 | 5/2015 |
| WO | 2016/196331 | 12/2016 |
| WO | 2016/196334 | 12/2016 |
| WO | 2016/196339 | 12/2016 |
| WO | 2016/197014 | 12/2016 |
| WO | 2016/197037 | 12/2016 |
| WO | 2017/204830 | 11/2017 |

OTHER PUBLICATIONS

Tynys et al., "Ethylene-Propylene Copolymerizations: Effect of Metallocene Structure on Termination Reactions and Polymer Miscrostructure," Macromolecular Chemical Phys., 2005, vol. 206, pp. 1043-1056.

U.S. Appl. No. 16/153,256 filed Oct. 5, 2018 Yang et al.

Mortazavi et al., "Characterization of MAO-Modified Silicas for Ethylene Polymerization," Journal of Applied Polymer Science, 2013, vol. 130, No. 6, pp. 4568-4575.

Chen et al., "Preparation and characterization of agglomerated porous hollow silica supports for olefin polymerization catalyst," Journal of Non-Crystalline Solids, 2007, vol. 353, No. 11-12, pp. 1030-1036.

Pasquini, N. (Ed.), Polypropylene Handbook, 2005, 2nd Ed., Hanser Publishers, Munich, pp. 78-89.

Shinamoto et al., "Microspherical Silica Supports with High Pore Volume for Metallocene Catalysts," presented at Metallocenes Europe '97 Dusseldorf, Germany, Apr. 8-9, 1997.

Smit et al., "Effects of Methylaluminoxane Immobilization on Silica on the Performance of Zirconocene Catalysts in Propylene Polymerization," Journal of Polymer Science: Part A: Polymer Chemistry, 2005, vol. 43, pp. 2734-2748.

Von Hohenesche et al., "Agglomerated non-porous silica nanoparticles as model carriers in polyethylene synthesis," Journal of Molecular Catalysis A: Chemical, Elsevier, Amsterdam, NL, 2004, vol. 221, No. 1-2, pp. 185-199.

Cecchin et al, "On the Mechanism of Polypropene Growth over $MgCl_2/TiCl_4$ Catalyst Systems," Macromolecular Chemistry and Physics, 2001, vol. 202, No. 10, pp. 1987-1994.

D'Agnillo et al., "Controlling Molecular Weight Distributions of Polyethylene by Combining Soluble Metallocene/MAO Catalysts," Journal of Polymer Science Part A: Polymer Chemistry, 1998, vol. 36, No. 5, pp. 831-840.

Zheng et al., "Fragmentation Behavior of Silica-Supported Metallocene/MAO Catalysts in the Early Stages of Olefin Polymerization," Macromolecules, 2005, vol. 35, No. 11, pp. 4673-4678.

(56) References Cited

OTHER PUBLICATIONS

Imhoff et al,, "Characterization of Methylalurninoxanes and Determination of Trimethylalurninum Using Proton NMR", Organometallics, 1998, vol. 17, pp. 1941-1945.

Kaminsky, "Highly Active Metallocene Catalysts for Olefin Polymerization," Journal of Chemical Society, Dalton Trans., 1998, pp. 1413-1418.

Sinn, "Proposals for Structure and Effect of Methylalurnoxane Based on Mass Balances and Phase Separation Experiments," Macromolecular Symposia, 1995, vol. 97, Issue 1, pp. 27-52.

Severn et al., Editors, Tailor-Made Polymers, 2008, p. 103.

U.S. Appl. No. 16/301,596, filed Nov. 14, 2018.

METALLOCENE CATALYST COMPOSITIONS AND POLYMERIZATION PROCESS THEREWITH

RELATED APPLICATIONS AND PATENTS

This application claims priority to and is a continuation in part of PCT/US2016/034784, filed May 27, 2016.

This invention relates to: 1) PCT Application PCT/US2016/034755 (WO2016/196331), entitled "Supported Metallocene Catalyst Systems for Polymerization;" 2) PCT Application PCT/US2016/034760 (WO2016/196334), entitled "Single Reactor Production of Polymers in Gas or Slurry Phase;" and 3) PCT Application PCT/US2016/034768 (WO2016/196339), entitled "Production of Heterophasic Polymers in Gas or Slurry Phase;" all of which were filed on May 27, 2016.

FIELD OF THE INVENTION

This invention relates to novel catalyst compounds, catalyst systems comprising asymmetric substituted indenyl groups and uses thereof.

BACKGROUND OF THE INVENTION

Olefin polymerization catalysts are of great use in industry. Hence, there is interest in finding new catalyst systems that increase the commercial usefulness of the catalyst and allow the production of polymers having improved properties.

Catalysts for olefin polymerization are often based on metallocenes as catalyst precursors, which are typically activated either with an alumoxane or with an activator containing a non-coordinating anion. Metallocene catalysts for propylene copolymers, however, have been limited by their inability to produce propylene-ethylene copolymers of high molecular weight or other desired properties. This has been observed for many metallocene structures, such as the syndiospecific $C_s$ symmetric $Me_2C(Cp)(Flu)ZrCl_2$, the aspecific $C_{2v}$ symmetric $Me_2Si(Flu)_2ZrCl_2$, and both the $C_2$ symmetric rac-$Me_2C(3-iPr-Ind)_2ZrCl_2$ and the fluxional (2-Ph-Ind)$_2$ZrCl$_2$ catalysts for elastomeric polypropylene. This deficit has also been found for the isospecific $C_2$ symmetric rac-$Me_2Si(2-Me-4,5-Benz-Ind)_2ZrCl_2$ and rac-$Me_2Si(2-Me-4-Ph-Ind)_2ZrCl_2$ (L. Resconi, C. Fritze, "Metallocene Catalysts for Propylene Polymerization" In Polypropylene Handbook (N. Pasquini, Ed.), Ch. 2.2, Hanser Publishers, Munic 2005). It is thought that, while the 2-Me substitution of this catalyst family suppresses the β-hydrogen transfer to the propylene monomer and thus prevents the formation of low molecular weight polymer, it fails to prevent the β-hydrogen transfer to the ethylene comonomer in case of the latter's presence. This β-hydrogen transfer to the ethylene comonomer becomes the favored chain termination mechanism and leads to the formation of low molecular weight propylene-ethylene copolymers (A. Tynys et al., Macromol. Chem. Phys. 2005, Vol. 206, pp. 1043-1056, "Ethylene-Propylene Copolymerizations: Effect of Metallocene Structure on Termination Reactions and Polymer Microstructure"). Exceptions have been found in some zirconocenes with bulky ligands, such as rac-$Me_2C(3-tBu-Ind)_2ZrCl_2$, which show a marked increase in molecular weight by ethylene incorporation. This catalyst, however, has shortcomings in terms of homopolymer molecular weight and activity.

Desirable metallocene catalysts for isotactic polypropylene production produce polypropylenes with high melting points. This thought to be due to high stereospecificity and/or regioselectivity in the polymer microstructure. Within the rac-$Alk_2Si(2-Alk-Ind)_2ZrCl_2$ catalyst family (Alk=Alkyl), the stereospecificity and regioselectivity is continuously being modified. For Example, EP 834 519 A1 relates to rac-$Me_2Si(2-Me-4-Ar-Ind)_2ZrCl_2$ type metallocenes for the production of rigid, high melting point polypropylenes with high stereoregularity and very low amounts of regio errors. However, these polypropylenes did not fare well under commercially relevant process conditions and suffered from low activity/productivity-levels.

US 2001/0053833 discloses metallocenes where the 2-position is substituted with an unsubstituted heteroaromatic ring or a heteroaromatic ring having at least one substituent bonded to the ring that produce propylene ethylene copolymers having less than desired melting points.

WO 01/058970 relates to impact copolymers having a high melting point and a good rubber content, produced by catalysts of the rac-$Me_2Si(2-Alk-4-Ar-Ind)_2ZrCl_2$ family when both alkyl substituents were iso-propyl groups. However, these catalysts suffer from activity issues.

WO 02/002576 discloses bridged metallocenes of the (2-Alkyl-4-Ph-Ind)$_2$ZrCl$_2$ family where the 2-positions can be isopropyl and the Ph substituents are substituted in the 3 and 5-positions, particularly with t-butyl. However, these catalysts also suffer from activity/productivity issues at commercial conditions.

WO 03/002583 discloses bridged metallocenes of the (2-Alkyl-4-Ph-Ind)$_2$ZrCl$_2$ family where the 2-positions may be substituted with isopropyl groups and the 4-positions are substituted with Ph group substituted at the 2-position, particularly with a phenyl group. However, these catalysts also suffer from activity/productivity issues at commercial conditions. In addition, these catalysts have relatively low Mw capabilities for isotactic homopolypropylene.

EP 1 250 365; WO 97/40075; and WO 03/045551 relate to bisindenyl metallocenes where substituents at the 2-positions of either of the indenyl ligands are branched or cyclicized in the α-position. However, these catalysts still have relatively limited Mw capabilities for isotactic homopolypropylene.

WO 04/106351 relates to bisindenyl metallocenes having substituents in the 2-positions of the indenyl ligands with the proviso that one ligand is unbranched or bound via a $sp^2$-hybridized carbon atom and the other ligand is branched in the α-position. However, these catalysts still have relatively limited Mw capabilities for isotactic homopolypropylene.

U.S. Pat. No. 8,507,706 discloses bisindenyl metallocenes where at least one 2-position on the indenyl groups is substituted with a group branched at the beta-position and the other 2-position is not branched at the alpha-position. US 2011/0230630 discloses similar metallocenes except that the group at the 2-position is branched in the beta-position and that the beta-carbon atom is a quarternary carbon atom and part of a non-cyclic hydrocarbon system.

U.S. Pat. No. 7,829,495 discloses alkyl substituted metallocenes having a " . . . $C_3$ or greater hydrocarbyl . . . substitutent bonded to either the LA or LB ring through a primary carbon atom . . . preferably an n-alkyl substituent . . . " (see column 4, lines 9-12). Further, in the Examples section, (n-propylcyclopentadienyl)(tetramethylcyclopentadienyl)zirconium dichloride combined with methylalumoxane and Davision™ 948 silica is used for ethylene hexene polymerization; bis(n-propyl cyclopentadienyl) zirconium dichloride combined with methylalumoxane and Davision™ 948 silica is used for ethylene hexene polymerization; and dimethylsilyl(flourenyl)(n-propyl cyclopentadienyl) zirconium dichloride combined with methylalumoxane and Davision silica is used for ethylene hexene polymerization.

US 2015/0025208, published Jan. 22, 2015, discloses bridged bisindenyl compounds where the 2-positions on the indene ($R^2$ and $R^8$) are not the same and the 4-positions on the indene ($R^4$ and $R^{10}$) are substituted phenyl groups, where at least one of $R^4$ and $R^{10}$ is a phenyl group substituted at the 3 and 5-position.

US 2005/0182266 discloses a process for preparing transition metal compounds having a specific substitution pattern, the corresponding transition metal compounds themselves and their use in the preparation of catalyst systems and also the use of the catalyst systems in the polymerization and copolymerization of olefins.

Other references of interest include: U.S. Pat. Nos. 6,051,727; 6,255,506; EP 0 576 970; U.S. Pat. Nos. 5,459,117; 5,532,396; 5,543,373; 5,585,509; 5,631,202;5,696,045; 5,700,886; 6,492,465; 6,150,481; 5,770,753; 5,786,432; 5,840,644; 6,242,544; 5,869,584; 6,399,533; 6,444,833; 6,559,252; 6,608,224; 6,635,779; 6,841,501; 6,878,786; 6,949,614; 6,953,829; 7,034,173; 7,141,527; 7,314,903; 7,342,078; 7,405,261; 7,452,949; 7,569,651; 7,615,597; 7,799,880; 7,964,679; 7,985,799; 8,222,356; 5,278,264; 5,276,208; 5,049,535; US 2011/0230630; WO 02/002575; WO 02/022575; WO 2003/002583; U.S. Pat. No. 7,122,498; US 2011/0230630; US 2010/0267907; EP 1 250 365; WO 97/9740075; WO 03/045551; WO 02/002576; US 2015/0025205; U.S. Ser. No. 14/572,195; filed Dec. 16, 2014; U.S. Pat. No. 9,193,856; WO 2004/052945; US 2016/0032025; and Journal of Molecular Catalysis A: Chemical (20010705), 172(1-2), pp. 43-65.

This invention relates to co-owned U.S. Pat. No. 9,249,239 and co-pending applications U.S. Ser. No. 15/000,731, filed Jan. 19, 2016; U.S. Ser. No. 14/324,333, filed Jul. 7, 2014; U.S. Ser. No. 14/324,408, filed Jul. 7, 2014; and U.S. Ser. No. 14/324,427, filed Jul. 7, 2014.

There is still a need in the art for new and improved catalyst systems for the polymerization of olefins, in order to achieve specific polymer properties, such as high melting point, high molecular weights, to increase conversion or comonomer incorporation, or to alter comonomer distribution without deteriorating the resulting polymer's properties.

It is therefore an object of the present invention to provide novel catalyst compounds, catalysts systems comprising such compounds, and processes for the polymerization of olefins using such compounds and systems.

Furthermore, it is an objective of the present invention to provide olefin polymers, particularly propylene homopolymers, and random copolymers of propylene with ethylene and/or higher alpha-olefins.

SUMMARY OF THE INVENTION

This invention relates to a process to polymerize propylene comprising contacting, at a temperature of 80° C. or more, propylene and optional comonomer with a homogeneous catalyst system comprising non-coordinating anion activator and one or more metallocene catalyst compounds represented by the formula:

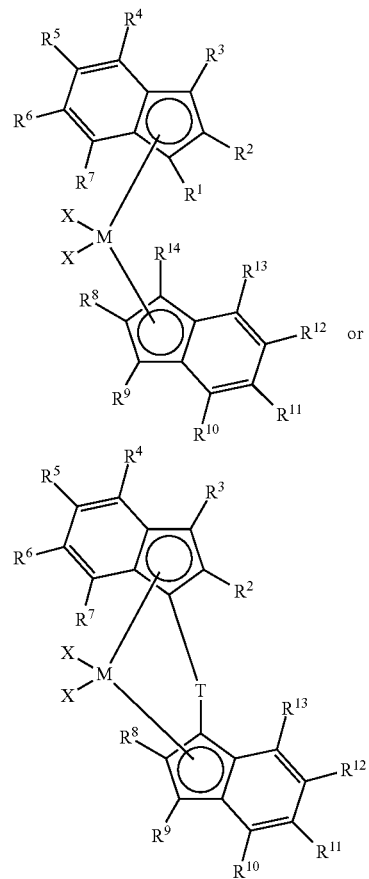

wherein, $R^2$ and $R^8$ are, independently, a $C_1$ to $C_{20}$ linear alkyl group, preferably at least one of $R^2$ and $R^8$ must have at least 4 carbon atoms;

$R^4$ and $R^{10}$ are substituted or unsubstituted aryl groups, provided that at least one of the aryl groups is: 1) substituted at an othro-position with at least one group selected from $C_1$ to $C_{40}$ hydrocarbyls, heteroatoms, and heteroatom containing groups and/or 2) substituted at the 3', 4' or 5'-position with at least one group selected from $C_1$ to $C_{40}$ hydrocarbyls, heteroatoms, and heteroatom containing groups;

M is a group 2, 3 or 4 transition metal;

T is a bridging group;

each X is an anionic leaving group; and each $R^1$, $R^3$, $R^5$, $R^6$, $R^7$, $R^9$, $R^{11}$, $R^{12}$, $R^{13}$, and $R^{14}$ is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, where the ethylene monomer is present a partial pressure of 0 to 6900 kPa.

DETAILED DESCRIPTION OF THE INVENTION

Figure 1:
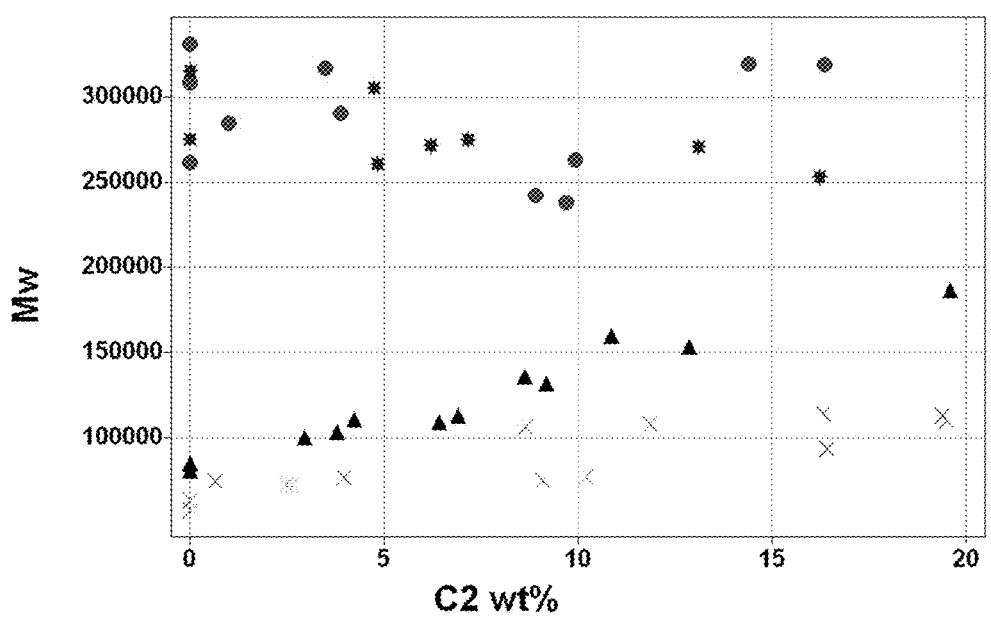
FIG. 1 shows a plot of weight average molecular weight (g/mol) versus ethylene content (wt %) for ethylene-propylene copolymer produced at 85° C. using catalysts prepared with metallocene and either B20 or B28 activator. Symbols Used: MCN-1/BF28 (circle), MCN-2/BF28 (star), MCN-3/BF28 (triangle), MCN-3/BF20 (saltire).

For the purposes of this invention and the claims thereto, the new numbering scheme for the Periodic Table Groups is used as described in CHEMICAL AND ENGINEERING NEWS, 63(5), p. 27 (1985). Therefore, a "Group 4 metal" is an element from Group 4 of the Periodic Table.

A homogeneous catalyst system is a system where the transition metal catalyst compound and the activator are dissolved in the polymerization medium, typically the catalyst system is not supported on a support and is dissolved in the solvent/monomer mixture.

Unless otherwise indicated, "catalyst activity" is a measure of how active the catalyst is and, unless otherwise indicated, is reported as the mass of product polymer produced per mole of catalyst used over a period of time. This may be given in units of (kg of polymer)/(mmol of catalyst) (minute). Other units of mass, molar quantity, or time may similarly be employed. Unless otherwise indicated, "conversion" is the amount of monomer that is converted to polymer product, and is reported as mol % and is calculated based on the polymer yield and the amount of monomer fed into the reactor.

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers and the like. An "ethylene polymer" or "ethylene copolymer" is a polymer or copolymer comprising at least 50 mol % ethylene derived units, a "propylene polymer" or "propylene copolymer" is a polymer or copolymer comprising at least 50 mol % propylene derived units, and so on.

For the purposes of this invention, ethylene shall be considered an α-olefin.

For purposes of this invention and claims thereto, the term "substituted" means that a hydrogen group has been replaced with a heteroatom, or a heteroatom containing group. For example, a "substituted hydrocarbyl" is a radical made of carbon and hydrogen where at least one hydrogen is replaced by a heteroatom or heteroatom containing group.

Unless otherwise indicated, room temperature is 23° C.

"Different" or "not the same" as used to refer to R groups in any formula herein (e.g., $R^2$ and $R^8$ or $R^4$ and $R^{10}$) or any substituent herein indicates that the groups or substituents differ from each other by at least one atom or are different isomerically.

As used herein, Mn is number average molecular weight, Mw is weight average molecular weight, and Mz is z average molecular weight, wt % is weight percent, and mol % is mole percent. Molecular weight distribution (MWD), also referred to as polydispersity index (PDI), is defined to be Mw divided by Mn. Unless otherwise noted, all molecular weight units (e.g., Mw, Mn, Mz) are reported in units of g/mol. The following abbreviations may be used herein: Me is methyl, Et is ethyl, Pr is propyl, cPr is cyclopropyl, nPr is n-propyl, iPr is isopropyl, Bu is butyl, nBu is normal butyl, iBu is isobutyl, sBu is sec-butyl, tBu is tert-butyl, Oct is octyl, Ph is phenyl, Bn is benzyl, MAO is methylalumoxane.

A "catalyst system" is the combination of at least one catalyst compound, at least one activator, and an optional co-activator. For the purposes of this invention and the claims thereto, when catalyst systems are described as comprising neutral stable forms of the components, it is well understood by one of ordinary skill in the art, that the ionic form of the component is the form that reacts with the monomers to produce polymers.

In the description herein, the metallocene catalyst may be described as a catalyst precursor, a pre-catalyst compound, metallocene catalyst compound or a transition metal compound, and these terms are used interchangeably. An "anionic ligand" is a negatively charged ligand which donates one or more pairs of electrons to a metal ion.

A metallocene catalyst is defined as an organometallic compound with at least one π-bound cyclopentadienyl moiety (or substituted cyclopentadienyl moiety) and more frequently two π-bound cyclopentadienyl moieties or substituted cyclopentadienyl moieties bonded to a transition metal.

For purposes of this invention and claims thereto in relation to metallocene catalyst compounds, the term "substituted" means that a hydrogen group has been replaced with a hydrocarbyl group, a heteroatom, or a heteroatom containing group. For example, methyl cyclopentadiene (Cp) is a Cp group substituted with a methyl group.

For purposes of this invention and claims thereto, "alkoxides" include those where the alkyl group is a $C_1$ to $C_{10}$ hydrocarbyl. The alkyl group may be straight chain, branched, or cyclic. The alkyl group may be saturated or unsaturated. In some embodiments, the alkyl group may comprise at least one aromatic group.

"Asymmetric" as used in connection with the instant indenyl compounds means that the substitutions at the 4-positions are different, or the substitutions at the 2-positions are different, or the substitutions at the 4-positions are different and the substitutions at the 2-positions are different.

Metallocene Catalyst Compounds

Metallocene catalyst compound useful herein include those represented by the formula:

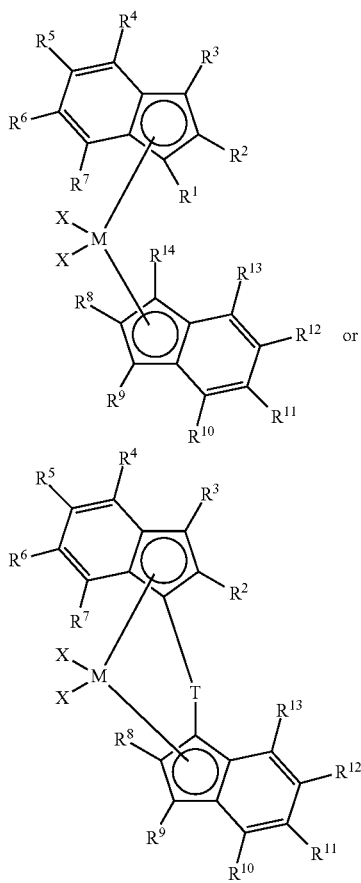

wherein,

R² and R⁸ are may be the same or different and each is, independently a $C_1$ to $C_{20}$ linear alkyl group, preferably at least one of R² and R⁸ has at least 4 carbon atoms, preferably at least 6 carbon atoms, preferably R² and R⁸ have no branches at the alpha or beta-positions;

R⁴ and R¹⁰ are substituted or unsubstituted aryl groups (such as substituted or unsubstituted phenyl groups, preferably substituted phenyl groups), provided that at least one of the aryl groups is: 1) substituted at an othro-position with at least one group selected from $C_1$ to $C_{40}$ hydrocarbyls, heteroatoms, and heteroatom containing groups and/or 2) substituted at the 3', 4' or 5'-position with at least one group selected from $C_1$ to $C_{40}$ hydrocarbyls, heteroatoms, and heteroatom containing groups;

M is a group 2, 3 or 4 transition metal, preferably group 4 transition metal;

T is a bridging group;

each X is an anionic leaving group; and each R¹, R³, R⁵, R⁶, R⁷, R⁹, R¹¹, R¹², R¹³, and R¹⁴ is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents.

In any embodiment described herein, R² may be a linear $C_1$-$C_{10}$ alkyl group, such as methyl, ethyl, n-propyl, n-butyl, n-pentyl, n-hexyl, n-heptyl, n-octyl, n-nonyl or n-decyl, which may be halogenated, preferably with I, F, Cl or Br.

In any embodiment described herein, R⁸ is a linear $C_1$-$C_{10}$ alkyl group, preferably methyl, ethyl, n-propyl, n-butyl, n-pentyl, n-hexyl, n-heptyl, n-octyl, n-nonyl or n-decyl, which may be halogenated, preferably with I, F, Cl or Br.

In some embodiments of the invention, R² and R⁸ are the same linear alkyl group, such as n-butyl, n-hexyl, etc.

In alternate embodiments, R² and R⁸ are different, such as R² is methyl and R⁸ is n-butyl, n-pentyl, n-hexyl, n-heptyl, or n-octyl.

By "substituted phenyl group" is meant a phenyl is substituted with 1, 2, 3, 4, or 5 $C_1$ to $C_{20}$ substituted or unsubstituted hydrocarbyl groups, such as methyl, ethyl, propyl, butyl, pentyl, hexyl, heptyl, octyl, nonyl, decyl, undecyl, dodecyl, phenyl, substituted phenyl, biphenyl or an isomer thereof. In useful embodiments, the phenyl group is substituted at the meta or para-positions, preferably the 3'- and/or 5'-positions, preferably with $C_4$ to $C_{12}$ alkyl groups. Alternately, the phenyl group may be substituted at the 2'-position, but is preferably not substituted in the 2'- and 6'-positions, e.g., in a preferred embodiment of the invention when the 2'-position of the phenyl is substituted, the 6'-position is H. Alternately, the phenyl group may be substituted at the 4'-position, with a group of the formula $(XR'_n)^-$, wherein X is a Group 14, 15, 16, or 17 heteroatom and R' is one of a hydrogen atom, halogen atom, a $C_1$-$C_{10}$ alkyl group, or a $C_6$-$C_{10}$ aryl group and n is 0, 1, 2, or 3; preferably —NR'₂, —SR', —OR', —OSiR'₃, —SiR'₃, or —PR'₂; and, optionally, one or more of the remaining positions on the phenyl are substituted, such as the 2', 3' and or 5'-positions.

In another aspect the 4'-position on the aryl group is not a $C_4$ group, alternately is not a hydrocarbyl group.

In another aspect, R⁴ and R¹⁰ are independently substituted phenyl groups, preferably phenyl groups substituted with $C_1$ to a $C_{10}$ alkyl groups (such as t-butyl, sec-butyl, n-butyl, isopropyl, n-propyl, cyclopropyl, cyclobutyl, cyclopentyl, cyclohexyl, cycloheptyl, cyclooctyl, phenyl, mesityl, or adamantyl), or an aryl group which may be further substituted with an aryl group, and the two aryl groups bound together can be joined together directly or by linker groups, wherein the linker group is an alkyl, vinyl, phenyl, alkynyl, silyl, germyl, amine, ammonium, phosphine, phosphonium, ether, thioether, borane, borate, alane or aluminate groups.

In another aspect, at least one of R⁴ and R¹⁰ is (or, optionally, both are) a phenyl group substituted at the 3' and 5'-position.

In another aspect, at least one of R⁴ and R¹⁰ is (or, optionally, both are) a phenyl group substituted at the 2'-position with an alkyl or an aryl group, such as a phenyl group.

In another aspect, at least one of R⁴ and R¹⁰ is (or, optionally, both are) a phenyl group substituted at the 3' and 5'-position and at least one of R⁴ and R¹⁰ is a phenyl group substituted at the 2'-position with an alkyl group or an aryl group, such as a phenyl group.

In yet another aspect, at least one of R⁴ and R¹⁰ is (or, optionally, both are) a phenyl group substituted at the 3' and 5'-positions with $C_1$ to a $C_{10}$ alkyl groups, such as a tertiary butyl group.

In yet another aspect, at least one of R⁴ and R¹⁰ is a phenyl group substituted at the 3' and 5'-positions with $C_1$ to a $C_{10}$ alkyl groups, such as a tertiary butyl group and at least one of R⁴ and R¹⁰ is a phenyl group substituted at the 2'-position with an alkyl or an aryl group, such as a phenyl group.

In yet another aspect, at least one of R⁴ and R¹⁰ is a phenyl group substituted at the 3' and 5'-positions with $C_1$ to a $C_{10}$ alkyl groups, such as a tertiary butyl group and at the 4'-position with $(XR'_n)^-$, wherein X is a Group 14, 15, 16 or 17 heteroatom having an atomic weight of 13 to 79, R' is one of a hydrogen atom, halogen atom, a $C_1$-$C_{10}$ alkyl group, or a $C_6$-$C_{10}$ aryl group, and n is 0, 1, 2, or 3, such as methoxy, and at least one of $R^4$ and $R^{10}$ is a phenyl group substituted at the 2'-position with an alkyl or an aryl group, such as a phenyl group.

In yet another aspect, both $R^4$ and $R^{10}$ are a phenyl group substituted at the 3' and 5'-positions with $C_1$ to a $C_{10}$ alkyl groups, such as a tertiary butyl group.

In still another aspect, at least one of $R^4$ and $R^{10}$ is a phenyl group substituted at the 3' and 5'-positions with aryl groups, such as substituted or unsubstituted phenyl groups.

In still another aspect, both $R^4$ and $R^{10}$ are a phenyl group substituted at the 3' and 5'-positions with aryl groups, such as substituted or unsubstituted phenyl groups.

In another aspect, at least one of $R^4$ and $R^{10}$ is an aryl group substituted at 3' and 5'-positions with $C_1$ to a $C_{10}$ alkyl groups (such as t-butyl, sec-butyl, n-butyl, isopropyl, n-propyl, cyclopropyl, cyclobutyl, cyclopentyl, cyclohexyl, cycloheptyl, cyclooctyl, phenyl, mesityl, or adamantyl) or aryl groups and combinations thereof, wherein, when $R^4$ or $R^{10}$ is a phenyl group which is further substituted with an aryl group, the two groups bound together can be joined together directly or by linker groups, wherein the linker group is an alkyl, vinyl, phenyl, alkynyl, silyl, germyl, amine, ammonium, phosphine, phosphonium, ether, thioether, borane, borate, alane or aluminate groups.

Alternately, when at least one of $R^4$ and $R^{10}$ is a phenyl group substituted at 3' and 5' positions, the phenyl group may also be substituted at the 4'-position, preferably with a substituent is selected from $(XR'_n)^-$, wherein X is a Group 14, 15, 16 or 17 heteroatom having an atomic weight of 13 to 79 (preferably N, O, S, P, or Si) and R' is one of a hydrogen atom, halogen atom, a $C_1$-$C_{10}$ alkyl group (such as methyl, ethyl, propyl, butyl, pentyl, hexyl, octyl, nonyl, decyl or an isomer thereof), or a $C_6$-$C_{10}$ aryl group and n is 0, 1, 2, or 3; preferably $(XR'_n)^-$ is —NR'$_2$, —SR', —OR', —OSiR'$_3$, —SiR'$_3$, or —PR'$_2$, preferably $(XR'_n)^-$ is —NR'$_2$, —SR', —OR', —OSiR'$_3$, or —PR'$_2$, preferably $(XR'_n)^-$ is —SR', —OR', or —OSiR'$_3$, preferably $(XR'_n)^-$ is —NR'$_2$ or —PR'$_2$, or preferably $(XR'_n)^-$ is –OR' m, preferably where R' is a $C_1$-$C_{10}$ alkyl group, particularly a methoxy, ethoxy, n-propoxy, isopropoxy, n-butoxy, iso-butoxy, sec-butoxy, or t-butoxy group, most particularly methoxy.

In yet another aspect, M is Hf, Ti and/or Zr, particularly Hf and/or Zr, particularly Zr.

Suitable radicals for the each of the groups $R^1$, $R^3$, $R^5$, $R^6$, $R^7$, $R^9$, $R^{11}$, $R^{12}$, $R^{13}$, and $R^{14}$ are independently selected from hydrogen or hydrocarbyl radicals including methyl, ethyl, ethenyl, and all isomers (including cyclics such as cyclohexyl) of propyl, butyl, pentyl, hexyl, heptyl, octyl, nonyl, decyl, undecyl, dodecyl, propenyl, butenyl, and from halocarbyls and all isomers of halocarbyls including perfluoropropyl, perfluorobutyl, perfluoroethyl, perfluoromethyl, and from substituted hydrocarbyl radicals and all isomers of substituted hydrocarbyl radicals including trimethylsilylpropyl, trimethylsilylmethyl, trimethylsilylethyl, and from phenyl, and all isomers of hydrocarbyl substituted phenyl including methylphenyl, dimethylphenyl, trimethylphenyl, tetramethylphenyl, pentamethylphenyl, diethylphenyl, triethylphenyl, propylphenyl, dipropylphenyl, tripropylphenyl, dimethylethylphenyl, dimethylpropylphenyl, dimethylbutylphenyl, dipropylmethylphenyl, and the like; from all isomers of halo substituted phenyl (where halo is, independently, fluoro, chloro, bromo and iodo) including halophenyl, dihalophenyl, trihalophenyl, tetrahalophenyl, and pentahalophenyl; and from all isomers of halo substituted hydrocarbyl substituted phenyl (where halo is, independently, fluoro, chloro, bromo and iodo) including halomethylphenyl, dihalomethylphenyl, (trifluoromethyl)phenyl, bis(triflouromethyl)phenyl; and from all isomers of benzyl, and all isomers of hydrocarbyl substituted benzyl including methylbenzyl, dimethylbenzyl.

In other embodiments of the invention, each X is, independently, selected from the group consisting of hydrocarbyl radicals having from 1 to 20 carbon atoms, hydrides, amides, alkoxides, sulfides, phosphides, halides, dienes, amines, phosphines, ethers, and a combination thereof (two X's may form a part of a fused ring or a ring system).

Suitable examples for X include chloride, bromide, fluoride, iodide, hydride, and $C_1$ to $C_{20}$ hydrocarbyls, preferably methyl, ethyl, propyl, butyl, pentyl, hexyl, phenyl, benzyl, and all isomers thereof, or two X together are selected from $C_4$ to $C_{10}$ dienes, preferably butadiene, methylbutadiene, pentadiene, methylpentadiene, dimethylpentadiene, hexadiene, methylhexadiene, dimethylhexadiene, or from $C_1$ to $C_{10}$ alkylidenes, preferably methylidene, ethylidene, propylidene, or from $C_3$ to $C_{10}$ alkyldiyls, preferably propandiyl, butandiyl, pentandiyl, and hexandiyl. In particular, X is chloride or methyl.

In any embodiment, T is a bridging group selected from R'$_2$C, R'$_2$Si, R'$_2$Ge, R'$_2$CCR'$_2$, R'$_2$CCR'$_2$CR'$_2$, R'C=CR', R'C=CR'CR'$_2$, R'$_2$CSiR'$_2$, R'$_2$SiSiR'$_2$, R'$_2$CSiR'$_2$CR'$_2$, R'$_2$SiCR'$_2$SiR'$_2$, R'C=CR'SiR'$_2$, R'$_2$CGeR'$_2$, R'$_2$GeGeR'$_2$, R'$_2$CGeR'$_2$CR'$_2$, R'$_2$GeCR'$_2$GeR'$_2$, R'$_2$SiGeR'$_2$, R'C=CR'GeR'$_2$, R'B, R'$_2$C—BR', R'$_2$C—BR'—CR'$_2$, R'N, R'$_2$C—NR', R'$_2$C—NR'—CR'$_2$, R'P, R'$_2$C—PR', and R'$_2$C—PR'—CR'$_2$ where R' is, independently, hydrogen, hydrocarbyl, substituted hydrocarbyl, halocarbyl, substituted halocarbyl, silylcarbyl, or germylcarbyl, and two or more R' on the same atom or on adjacent atoms may join together to form a substituted or unsubstituted, saturated, partially unsaturated, or aromatic cyclic or polycyclic substituent.

Suitable examples for the bridging group T include dihydrocarbylsilylenes including dimethylsilylene, diethylsilylene, dipropylsilylene, dibutylsilylene, dipentylsilylene, dihexylsilylene, methylphenylsilylene, diphenylsilylene, dicyclohexylsilylene, methylcyclohexylsilylene, dibenzylsilylene, tetramethyldisilylene, cyclotrimethylenesilylene, cyclotetramethylenesilylene, cyclopentamethylenesilylene, divinylsilylene, and tetramethyldisiloxylene; dihydrocarbylgermylenes including dimethylgermylene, diethylgermylene, dipropylgermylene, dibutylgermylene, methylphenylgermylene, diphenylgermylene, dicyclohexylgermylene, methylcyclohexylgermylene, cyclotrimethylenegermylene, cyclotetramethylenegermylene, and cyclopentamethylenegermylene; carbylenes and carbdiyls including methylene, dimethylmethylene, diethylmethylene, dibutylmethylene, dipropylmethylene, diphenylmethylene, ditolylmethylene, di(butylphenyl)methylene, di(trimethylsilylphenyl)methylene, dibenzylmethylene, cyclotetramethylenemethylene, cyclopentamethylenemethylene, ethylene, methylethylene, dimethylethylene, trimethylethylene, tetramethylethylene, cyclopropylene, cyclobutylene, cyclopentylene, cyclohexylene, propanediyl, methylpropanediyl, dimethylpropanediyl, trimethylpropanediyl, tetramethylpropanediyl, pentamethylpropanediyl, hexamethylpropanediyl, vinylene, and ethene-1,1-diyl; boranediyls including methylboranediyl, ethylboranediyl, propylboranediyl, butylboranediyl, pentylboranediyl, hexylboranediyl, cyclohexylboranediyl, and phenylboranediyl; and combinations thereof including dimethylsilylmethylene, diphenylsilylmethylene, dimethylsilylethylene, methylphenylsilylmethylene.

In particular, T is $CH_2$, $CH_2CH_2$, $C(CH_3)_2$, $SiMe_2$, $SiPh_2$, $SiMePh$, $Si(CH_2)_3$, $Si(CH_2)_4$, $Si(Me_3SiPh)_2$, or $Si(CH_2)_5$.

In another embodiment, T is represented by the formula $R_2^a J$, where J is C, Si, or Ge, and each $R^a$ is, independently, hydrogen, halogen, $C_1$ to $C_{20}$ hydrocarbyl or a $C_1$ to $C_{20}$ substituted hydrocarbyl, and two $R^a$ can form a cyclic structure including aromatic, partially saturated, or saturated cyclic or fused ring system.

In a preferred embodiment of the invention in any formula described herein, T is represented by the formula, $(R^*_2 G)_g$, where each G is C, Si, or Ge, g is 1 or 2, and each $R^*$ is, independently, hydrogen, halogen, $C_1$ to $C_{20}$ hydrocarbyl or a $C_1$ to $C_{20}$ substituted hydrocarbyl, and two or more $R^*$ can form a cyclic structure including aromatic, partially saturated, or saturated cyclic or fused ring system.

In aspects of the invention, the rac/meso ratio of the metallocene catalyst is 50:1 or greater, or 40:1 or greater, or 30:1 or greater, or 20:1 or greater, or 15:1 or greater, or 10:1 or greater, or 7:1 or greater, or 5:1 or greater.

In an embodiment of the invention, the metallocene catalyst comprises greater than 55 mol % of the racemic isomer, or greater than 60 mol % of the racemic isomer, or greater than 65 mol % of the racemic isomer, or greater than 70 mol % of the racemic isomer, or greater than 75 mol % of the racemic isomer, or greater than 80 mol % of the racemic isomer, or greater than 85 mol % of the racemic isomer, or greater than 90 mol % of the racemic isomer, or greater than 92 mol % of the racemic isomer, or greater than 95 mol % of the racemic isomer, or greater than 98 mol % of the racemic isomer, based on the total amount of the racemic and meso isomer-if any, formed. In a particular embodiment of the invention, the metallocene, especially the bridged bis(indenyl)metallocene, compound consists essentially of the racemic isomer.

Amounts of rac and meso isomers are determined by proton NMR. 1H NMR data are collected at 23° C. in a 5 mm probe using a 400 MHz Bruker spectrometer with deuterated methylene chloride or deuterated benzene. Data is recorded using a maximum pulse width of 45°, 8 seconds between pulses and signal averaging 16 transients. The spectrum is normalized to protonated methylene chloride in the deuterated methylene chloride, which is expected to show a peak at 5.32 ppm.

In a preferred embodiment in any of the processes described herein one catalyst compound is used, e.g., the catalyst compounds are not different. For purposes of this invention one metallocene catalyst compound is considered different from another if they differ by at least one atom. For example, "bisindenyl zirconium dichloride" is different from "(indenyl)(2-methylindenyl) zirconium dichloride" which is different from "(indenyl)(2-methylindenyl) hafnium dichloride." Catalyst compounds that differ only by isomer are considered the same for purposes if this invention, e.g., rac-dimethylsilylbis(2-methyl 4-phenyl)hafnium dimethyl is considered to be the same as meso-dimethylsilylbis(2-methyl 4-phenyl)hafnium dimethyl.

In some embodiments, two or more different catalyst compounds are present in the catalyst system used herein. In some embodiments, two or more different catalyst compounds are present in the reaction zone where the process(es) described herein occur. When two transition metal compound based catalysts are used in one reactor as a mixed catalyst system, the two transition metal compounds should be chosen such that the two are compatible. A simple screening method such as by 1H or $^{13}C$ NMR, known to those of ordinary skill in the art, can be used to determine which transition metal compounds are compatible. It is preferable to use the same activator for the transition metal compounds, however, two different activators, such as a non-coordinating anion activator and an alumoxane, can be used in combination. If one or more transition metal compounds contain an $X_1$ or $X_2$ ligand which is not a hydride, hydrocarbyl, or substituted hydrocarbyl, then the alumoxane is typically contacted with the transition metal compounds prior to addition of the non-coordinating anion activator.

The transition metal compounds (pre-catalysts) may be used in any ratio. Preferred molar ratios of (A) transition metal compound to (B) transition metal compound fall within the range of (A:B) 1:1000 to 1000:1, alternatively 1:100 to 500:1, alternatively 1:10 to 200:1, alternatively 1:1 to 100:1, and alternatively 1:1 to 75:1, and alternatively 5:1 to 50:1. The particular ratio chosen will depend on the exact pre-catalysts chosen, the method of activation, and the end product desired. In a particular embodiment, when using the two pre-catalysts, where both are activated with the same activator, useful mole percents, based upon the molecular weight of the pre-catalysts, are 10 to 99.9% A to 0.1 to 90% B, alternatively 25 to 99% A to 0.5 to 50% B, alternatively 50 to 99% A to 1 to 25% B, and alternatively 75 to 99% A to 1 to 10% B.

In a preferred embodiment, T is dialkylsilyl, $R^2$ is methyl, $R^8$ is butyl, and $R^5$ and $R^6$ are joined to form a non-aromatic ring containing 5 or 6 or 7 atoms.

In a preferred embodiment, M is zirconium, T is dialkylsilyl, $R^2$ is methyl, and $R^5$ and $R^6$ are joined to form a ring containing 5 or 6 or 7 atoms.

In a preferred embodiment, T is dialkylsilyl, $R^2$ is methyl, $R^8$ is an unbranched alkyl group containing 2 to 14 carbons, and $R^5$ and $R^6$ are joined to form a ring containing 5 or 6 or 7 atoms.

In a preferred embodiment, M is zirconium, T is dialkylsilyl, $R^2$ is methyl, $R^8$ is an unbranched alkyl group containing 2 to 14 carbons, and $R^5$ and $R^6$ are joined to form a ring containing 5 or 6 or 7 atoms.

Methods to Prepare the Catalyst Compounds

Generally, metallocenes of this type are synthesized as shown in FIG. 13 of PCT/US2016/034784, filed May 27, 2016 where (i) is a deprotonation via a metal salt of alkyl anion (e.g., $^n$BuLi) to form an indenide; (ii) reaction of indenide with an appropriate bridging precursor (e.g., $Me_2SiCl_2$); (iii) reaction of the above product with AgOTf; (iv) reaction of the above triflate compound with another equivalent of indenide; (v) double deprotonation via an alkyl anion (e.g. $^n$BuLi) to form a dianion; and (vi) reaction of the dianion with a metal halide (e.g., $ZrCl_4$ or $HfCl_4$). The dichloride products are obtained by recrystallization of the crude solids where $Ar_1$ and $Ar_2$ are as defined for $R^4$ and $R^{10}$, and $R_1$ and $R_2$ are defined for $R^2$ and $R^8$.

The final dimethyl compounds are obtained by reacting above dichloride compounds with MeMgBr or MeLi.

Catalyst compounds useful herein include:
$Me_2Si(4-oPh_2-2-nC_6-Ind)(2-Me-4-(3',5'-tBu_2-4'-OMe-Ph)-Ind)ZrCl_2$; $Me_2Si(4-oPh_2-2-nBu-Ind)(2-Me-4-(3',5'-tBu_2-4'-OMe-Ph)-Ind)ZrCl_2$; $Me_2Si(4-oPh_2-2-nC_5-Ind)(2-Me-4-(3',5'-tBu_2-4'-OMe-Ph)-Ind)ZrCl_2$; $Me_2Si(4-oPh_2-2-nC_7-Ind)(2-Me-4-(3',5'-tBu_2-4'-OMe-Ph)-Ind)ZrCl_2$; $Me_2Si(4-oPh_2-2-nC_8-Ind)(2-Me-4-(3',5'-tBu_2-4'-OMe-Ph)-Ind)ZrCl_2$; $Me_2Si(4-oPh_2-2-nC_9-Ind)(2-Me-4-(3',5'-tBu_2-4'-OMe-Ph)-Ind)ZrCl_2$; $Me_2Si(4-oPh_2-2-nC_{10}-Ind)(2-Me-4-(3',5'-tBu_2-4'-OMe-Ph)-Ind)ZrCl_2$; $Me_2Si(4-oPh_2-2-nC_6-Ind)(2-Me-4-(3',5'-tBu_2Ph)-Ind)ZrCl_2$; $Me_2Si(4-oPh_2-2-nBu-Ind)(2-Me-4-(3',5'-tBu_2Ph)-Ind)ZrCl_2$; $Me_2Si(4-oPh_2-2-nC_5-Ind)(2-Me-4-(3',5'-tBu_2Ph)-Ind)ZrCl_2$; $Me_2Si(4-oPh_2-2-nC_7-Ind)(2-Me-4-(3',5'-tBu_2Ph)-Ind)ZrCl_2$; $Me_2Si(4-oPh_2-2-nC_8-Ind)(2-Me-4-(3',5'-tBu_2Ph)-Ind)ZrCl_2$; $Me_2Si(4-oPh_2-2-nC_9-Ind)(2-Me-4-(3',5'-tBu_2Ph)-Ind)$ ZrCl$_2$; Me$_2$Si(4-oPh$_2$-2-nC$_{10}$-Ind)(2-Me-4-(3',5'-tBu$_2$Ph)-Ind)ZrCl$_2$; Me$_2$Si(4-oPh$_2$-2-nC$_6$-Ind)(2-Me-4-(3',5'-tBu$_2$-4'-OMe-Ph)-Ind)ZrCl$_2$; Me$_2$Si(4-oPh$_2$-2-nBu-Ind)(2-Me-4-(3',5'-tBu$_2$-4'-OMe-Ph)-Ind)ZrCl$_2$; Me$_2$Si(4-oPh$_2$-2-nC$_5$-Ind)(2-Me-4-(3',5'-tBu$_2$-4'-OMe-Ph)-Ind)ZrCl$_2$; Me$_2$Si(4-oPh$_2$-2-nC$_7$-Ind)(2-Me-4-(3',5'-tBu$_2$-4'-OMe-Ph)-Ind)ZrCl$_2$; Ph$_2$Si(4-oPh$_2$-2-nC$_8$-Ind)(2-Me-4-(3',5'-tBu$_2$-4'-OMe-Ph)-Ind)ZrCl$_2$; Me$_2$Si(4-oPh$_2$-2-nC$_9$-Ind)(2-Me-4-(3',5'-tBu$_2$-4'-OMe-Ph)-Ind)ZrCl$_2$; Me$_2$Si(4-oPh$_2$-2-nC$_{10}$-Ind)(2-Me-4-(3',5'-tBu$_2$-4'-OMe-Ph)-Ind)ZrCl$_2$; Me$_2$Si(4-oPh$_2$-2-nC$_6$-Ind)(2-Me-4-(3',5'-tBu$_2$Ph)-Ind)ZrCl$_2$; Me$_2$Si(4-oPh$_2$-2-nBu-Ind)(2-Me-4-(3',5'-tBu$_2$Ph)-Ind)ZrCl$_2$; Me$_2$Si(4-oPh$_2$-2-nC$_5$-Ind)(2-Me-4-(3',5'-tBu$_2$Ph)-Ind)ZrCl$_2$; Me$_2$Si(4-oPh$_2$-2-nC$_7$-Ind)(2-Me-4-(3',5'-tBu$_2$Ph)-Ind)ZrCl$_2$; Me$_2$Si(4-oPh$_2$-2-nC$_8$-Ind)(2-Me-4-(3',5'-tBu$_2$Ph)-Ind)ZrCl$_2$; Me$_2$Si(4-oPh$_2$-2-nC$_9$-Ind)(2-Me-4-(3',5'-tBu$_2$Ph)-Ind)ZrCl$_2$; Me$_2$Si(4-oPh$_2$-2-nC$_{10}$-Ind)(2-Me-4-(3',5'-tBu$_2$Ph)-Ind)ZrCl$_2$; Me$_2$Si(4-oPh$_2$-2-nC$_6$-Ind)(2-Et-4-(3',5'-tBu$_2$-4'-OMe-Ph)-Ind)ZrCl$_2$; Me$_2$Si(4-oPh$_2$-2-nBu-Ind)(2-Et-4-(3',5'-tBu$_2$-4'-OMe-Ph)-Ind)ZrCl$_2$; Me$_2$Si(4-oPh$_2$-2-nC$_5$-Ind)(2-Et-4-(3',5'-tBu$_2$-4'-OMe-Ph)-Ind)ZrCl$_2$; Me$_2$Si(4-oPh$_2$-2-nC$_7$-Ind)(2-Et-4-(3',5'-tBu$_2$-4'-OMe-Ph)-Ind)ZrCl$_2$; Me$_2$Si(4-oPh$_2$-2-nC$_8$-Ind)(2-Et-4-(3',5'-tBu$_2$-4'-OMe-Ph)-Ind)ZrCl$_2$; Me$_2$Si(4-oPh$_2$-2-nC$_9$-Ind)(2-Et-4-(3',5'-tBu$_2$-4'-OMe-Ph)-Ind)ZrCl$_2$; Me$_2$Si(4-oPh$_2$-2-nC$_{10}$-Ind)(2-Et-4-(3',5'-tBu$_2$-4'-OMe-Ph)-Ind)ZrCl$_2$; Me$_2$Si(4-oPh$_2$-2-nC$_6$-Ind)(2-Et-4-(3',5'-tBu$_2$Ph)-Ind)ZrCl$_2$; Me$_2$Si(4-oPh$_2$-2-nBu-Ind)(2-Et-4-(3',5'-tBu$_2$Ph)-Ind)ZrCl$_2$; Me$_2$Si(4-oPh$_2$-2-nC$_5$-Ind)(2-Et-4-(3',5'-tBu$_2$Ph)-Ind)ZrCl$_2$; Me$_2$Si(4-oPh$_2$-2-nC$_7$-Ind)(2-Et-4-(3',5'-tBu$_2$Ph)-Ind)ZrCl$_2$; Me$_2$Si(4-oPh$_2$-2-nC$_8$-Ind)(2-Et-4-(3',5'-tBu$_2$Ph)-Ind)ZrCl$_2$; Me$_2$Si(4-oPh$_2$-2-nC$_9$-Ind)(2-Et-4-(3',5'-tBu$_2$Ph)-Ind)ZrCl$_2$; Me$_2$Si(4-oPh$_2$-2-nC$_{10}$-Ind)(2-Et-4-(3',5'-tBu$_2$Ph)-Ind)ZrCl$_2$; Me$_2$Si(4-oPh$_2$-2-nC$_6$-Ind)(2-nPr-4-(3',5'-tBu$_2$-4'-OMe-Ph)-Ind)ZrCl$_2$; Me$_2$Si(4-oPh$_2$-2-nBu-Ind)(2-nPr-4-(3',5'-tBu$_2$-4'-OMe-Ph)-Ind)ZrCl$_2$; Me$_2$Si(4-oPh$_2$-2-nC$_5$-Ind)(2-Et-4-(3',5'-tBu$_2$-4'-OMe-Ph)-Ind)ZrCl$_2$; Me$_2$Si(4-oPh$_2$-2-nC$_7$-Ind)(2-Et-4-(3',5'-tBu$_2$-4'-OMe-Ph)-Ind)ZrCl$_2$; Me$_2$Si(4-oPh$_2$-2-nC$_8$-Ind)(2-Et-4-(3',5'-tBu$_2$-4'-OMe-Ph)-Ind)ZrCl$_2$; Me$_2$Si(4-oPh$_2$-2-nC$_9$-Ind)(2-Et-4-(3',5'-tBu$_2$-4'-OMe-Ph)-Ind)ZrCl$_2$; Me$_2$Si(4-oPh$_2$-2-nC$_{10}$-Ind)(2-Et-4-(3',5'-tBu$_2$-4'-OMe-Ph)-Ind)ZrCl$_2$; Me$_2$Si(4-oPh$_2$-2-nC$_6$-Ind)(2-Et-4-(3',5'-tBu$_2$Ph)-Ind)ZrCl$_2$; Me$_2$Si(4-oPh$_2$-2-nBu-Ind)(2-Et-4-(3',5'-tBu$_2$Ph)-Ind)ZrCl$_2$; Me$_2$Si(4-oPh$_2$-2-nC$_5$-Ind)(2-Et-4-(3',5'-tBu$_2$Ph)-Ind)ZrCl$_2$; Me$_2$Si(4-oPh$_2$-2-nC$_7$-Ind)(2-Et-4-(3',5'-tBu$_2$Ph)-Ind)ZrCl$_2$; Me$_2$Si(4-oPh$_2$-2-nC$_8$-Ind)(2-Et-4-(3',5'-tBu$_2$Ph)-Ind)ZrCl$_2$; Me$_2$Si(4-oPh$_2$-2-nC$_9$-Ind)(2-Et-4-(3',5'-tBu$_2$Ph)-Ind)ZrCl$_2$; Me$_2$Si(4-oPh$_2$-2-nC$_{10}$-Ind)(2-Et-4-(3',5'-tBu$_2$Ph)-Ind)ZrCl$_2$; Me$_2$Si(4-oPh$_2$-2-nC$_6$-Ind)(2-Et-4-(3',5'-tBu$_2$-4'-OMe-Ph)-Ind)ZrCl$_2$; Me$_2$Si(4-oPh$_2$-2-nBu-Ind)(2-Et-4-(3',5'-tBu$_2$-4'-OMe-Ph)-Ind)ZrCl$_2$; Me$_2$Si(4-oPh$_2$-2-nC$_5$-Ind)(2-Et-4-(3',5'-tBu$_2$-4'-OMe-Ph)-Ind)ZrCl$_2$; Me$_2$Si(4-oPh$_2$-2-nC$_7$-Ind)(2-Et-4-(3',5'-tBu$_2$-4'-OMe-Ph)-Ind)ZrCl$_2$; Me$_2$Si(4-oPh$_2$-2-nC$_8$-Ind)(2-Et-4-(3',5'-tBu$_2$-4'-OMe-Ph)-Ind)ZrCl$_2$; Me$_2$Si(4-oPh$_2$-2-nC$_9$-Ind)(2-n-propyl-4-(3',5'-tBu$_2$-4'-OMe-Ph)-Ind)ZrCl$_2$; Me$_2$Si(4-oPh$_2$-2-nC$_{10}$-Ind)(2-nC$_3$-4-(3',5'-tBu$_2$-4'-OMe-Ph)-Ind)ZrCl$_2$; Me$_2$Si(4-oPh$_2$-2-nC$_6$-Ind)(2-nC$_3$-4-(3',5'-tBu$_2$Ph)-Ind)ZrCl$_2$; Me$_2$Si(4-oPh$_2$-2-nBu-Ind)(2-nPr-4-(3',5'-tBu$_2$Ph)-Ind)ZrCl$_2$; Me$_2$Si(4-oPh$_2$-2-nC$_5$-Ind)(2-nPr-4-(3',5'-tBu$_2$Ph)-Ind)ZrCl$_2$; Me$_2$Si(4-oPh$_2$-2-nC$_7$-Ind)(2-n-propyl-4-(3',5'-tBu$_2$Ph)-Ind)ZrCl$_2$; Me$_2$Si(4-oPh$_2$-2-nC$_8$-Ind)(2-n-propyl-4-(3',5'-tBu$_2$Ph)-Ind)ZrCl$_2$; Me$_2$Si(4-oPh$_2$-2-nC$_9$-Ind)(2-nC$_3$-4-(3',5'-tBu$_2$Ph)-Ind)ZrCl$_2$; Me$_2$Si(4-oPh$_2$-2-nC$_{10}$-Ind)(2-n-propyl-4-(3',5'-tBu$_2$Ph)-Ind)ZrCl$_2$; Me$_2$Si(4-oPh$_2$-2-nC$_6$-Ind)$_2$ZrCl$_2$; Me$_2$Si(4-oPh$_2$-2-nC$_5$-Ind)$_2$ZrCl$_2$; Me$_2$Si(4-oPh$_2$-2-nBu-Ind)$_2$ZrCl$_2$; Me$_2$Si(4-oPh$_2$-2-nC$_7$-Ind)$_2$ZrCl$_2$; Me$_2$Si$_2$(4-oPh$_2$-2-nC$_8$-Ind)$_2$ZrCl$_2$; Me$_2$Si(4-oPh$_2$-2-nC$_9$-Ind)$_2$ZrCl$_2$; Me$_2$Si(4-oPh$_2$-2-nC$_{10}$-Ind)$_2$ZrCl$_2$; Me$_2$Si(2-nBu-4-(3',5'-tBu$_2$-4'-OMe-Ph)-Ind)$_2$ZrCl$_2$; Me$_2$Si(2-nC$_5$-4-(3',5'-tBu$_2$-4'-OMe-Ph)-Ind)$_2$ZrCl$_2$; Me$_2$Si$_2$(2-n-hexyl-4-(3',5'-tBu$_2$-4'-OMe-Ph)-Ind)$_2$ZrCl$_2$; Me$_2$Si(2-nC$_7$-4-(3',5'-tBu$_2$-4'-OMe-Ph)-Ind)$_2$ZrCl$_2$; Me$_2$Si(2-nC$_8$-4-(3',5'-tBu$_2$-4'-OMe-Ph)-Ind)$_2$ZrCl$_2$; Me$_2$Si(2-nC$_9$-4-(3',5'-tBu$_2$-4'-OMe-Ph)-Ind)$_2$ZrCl$_2$; Me$_2$Si(2-nC$_{10}$-4-(3',5'-tBu$_2$-4'-OMe-Ph)-Ind)$_2$ZrCl$_2$; Me$_2$Si(2-nBu-4-(3',5'-tBu$_2$Ph)-Ind)$_2$ZrCl$_2$; Me$_2$Si(2-nC$_5$-4-(3',5-tBu$_2$Ph)-Ind)$_2$ZrCl$_2$; Me$_2$Si(2-n-hexyl-4-(3',5'-tBu$_2$Ph)-Ind)$_2$ZrCl$_2$; Me$_2$Si(2-nC$_7$-4-(3',5-tBu$_2$Ph)-Ind)$_2$ZrCl$_2$; Me$_2$Si(2-nC$_8$-4-(3',5'-tBu$_2$Ph)-Ind)$_2$ZrCl$_2$; Me$_2$Si(2-nC$_9$-4-(3',5'-tBu$_2$Ph)-Ind)$_2$ZrCl$_2$; Me$_2$Si(2-nC$_{10}$-4-(3,5'-tBu$_2$Ph)-Ind)$_2$ZrCl$_2$; Me$_2$Si(2-Me-4-(3',5'-tBu$_2$-4'-OMe-Ph)-Ind)(2-nBu-4-(3',5'-tBu$_2$-4'-OMe-Ph)-Ind)ZrCl$_2$; Me$_2$Si(2-Me-4-(3',5'-tBu$_2$-4'-OMe-Ph)-Ind)(2-nC$_5$-4-(3',5'-tBu$_2$-4'-OMe-Ph)-Ind)ZrCl$_2$; Me$_2$Si(2-Me-4-(3',5'-tBu$_2$-4'-OMe-Ph)-Ind)(2-n-hexyl-4-(3',5'-tBu$_2$-4'-OMe-Ph)-Ind)ZrCl$_2$; Me$_2$Si(2-Me-4-(3',5'-tBu$_2$-4'-OMe-Ph)-Ind)(2-nC$_7$-4-(3',5'-tBu$_2$-4'-OMe-Ph)-Ind)ZrCl$_2$; Me$_2$Si(2-Me-4-(3',5'-tBu$_2$-4'-OMe-Ph)-Ind)(2-nC$_8$-4-(3',5'-tBu$_2$-4'-OMe-Ph)-Ind)ZrCl$_2$; Me$_2$Si(2-Me-4-(3',5'-tBu$_2$-4'-OMe-Ph)-Ind)(2-nC$_9$-4-(3',5'-tBu$_2$-4'-OMe-Ph)-Ind)ZrCl$_2$; Me$_2$Si(2-Me-4-(3',5'-tBu$_2$-4'-OMe-Ph)-Ind)(2-nC$_{10}$-4-(3',5'-tBu$_2$-4'-OMe-Ph)-Ind)ZrCl$_2$; Me$_2$Si(2-Me-4-(3',5'-tBu$_2$Ph)-Ind)(2-nBu-4-(3',5'-tBu$_2$Ph)-Ind)ZrCl$_2$; Me$_2$Si(2-Me-4-(3',5'-tBu$_2$Ph)-Ind)(2-nC$_5$-4-(3',5'-tBu$_2$Ph)-Ind)ZrCl$_2$; Me$_2$Si(2-Me-4-(3',5'-tBu$_2$Ph)-Ind)(2-n-hexyl-4-(3',5'-tBu$_2$Ph)-Ind)ZrCl$_2$; Me$_2$Si(2-Me-4-(3',5'-tBu$_2$Ph)-Ind)(2-nC$_7$-4-(3',5'-tBu$_2$Ph)-Ind)ZrCl$_2$; Me$_2$Si(2-Me-4-(3',5'-tBu$_2$Ph)-Ind)(2-nC$_8$-4-(3',5'-tBu$_2$Ph)-Ind)ZrCl$_2$; Me$_2$Si(2-Me-4-(3',5'-tBu$_2$Ph)-Ind)(2-nC$_9$-4-(3',5'-tBu$_2$Ph)-Ind)ZrCl$_2$; Me$_2$Si(2-Me-4-(3',5'-tBu$_2$Ph)-Ind)(2-nC$_{10}$-4-(3',5'-tBu$_2$Ph)-Ind)ZrCl$_2$; Me$_2$Si(4-oPh$_2$-2-Me-Ind)(4-oPh$_2$-2-nBu-Ind)ZrCl$_2$; Me$_2$Si(4-oPh$_2$-2-Me-Ind)(4-oPh$_2$-2-nC$_5$-Ind)ZrCl$_2$; Me$_2$Si(4-oPh$_2$-2-Me-Ind)(4-oPh$_2$-2-nC$_6$-Ind)ZrCl$_2$; Me$_2$Si(4-oPh$_2$-2-Me-Ind)(4-oPh$_2$-2-nC$_7$-Ind)ZrCl$_2$; Me$_2$Si(4-oPh$_2$-2-Me-Ind)(4-oPh$_2$-2-nC$_8$-Ind)ZrCl$_2$; Me$_2$Si(4-oPh$_2$-2-Me-Ind)(4-oPh$_2$-2-nC$_9$-Ind)ZrCl$_2$; Me$_2$Si(4-oPh$_2$-2-Me-Ind)(4-oPh$_2$-2-nC$_{10}$-Ind)ZrCl$_2$; Me$_2$Si(4-oPh$_2$-2-Et-Ind)(4-oPh$_2$-2-nBu-Ind)ZrCl$_2$; Me$_2$Si(4-oPh$_2$-2-Et-Ind)(4-oPh$_2$-2-nC$_5$-Ind)ZrCl$_2$; Me$_2$Si(4-oPh$_2$-2-Et-Ind)(4-oPh$_2$-2-nC$_6$-Ind)ZrCl$_2$; Me$_2$Si(4-oPh$_2$-2-Et-Ind)(4-oPh$_2$-2-nC$_7$-Ind)ZrCl$_2$; Me$_2$Si(4-oPh$_2$-2-Et-Ind)(4-oPh$_2$-2-nC$_8$-Ind)ZrCl$_2$; Me$_2$Si(4-oPh$_2$-2-Et-Ind)(4-oPh$_2$-2-nC$_9$-Ind)ZrCl$_2$; Me$_2$Si(4-oPh$_2$-2-Et-Ind)(4-oPh$_2$-2-nC$_{10}$-Ind)ZrCl$_2$; Me$_2$Si(4-oPh$_2$-2-n-propyl-Ind)(4-oPh$_2$-2-nBu-Ind)ZrCl$_2$; Me$_2$Si(4-oPh$_2$-2-n-propyl-Ind)(4-oPh$_2$-2-nC$_5$-Ind)ZrCl$_2$; Me$_2$Si(4-oPh$_2$-2-n-propyl-Ind)(4-oPh$_2$-2-nC$_6$-Ind)ZrCl$_2$; Me$_2$Si(4-oPh$_2$-2-n-propyl-Ind)(4-oPh$_2$-2-nC$_7$-Ind)ZrCl$_2$; Me$_2$Si(4-oPh$_2$-2-n-propyl-Ind)(4-oPh$_2$-2-nC$_8$-Ind)ZrCl$_2$; Me$_2$Si(4-oPh$_2$-2-nPr-Ind)(4-oPh$_2$-2-nC$_9$-Ind)ZrCl$_2$; Me$_2$Si(4-oPh$_2$-2-nPr-Ind)(4-oPh$_2$-2- nC$_{10}$-Ind)ZrCl$_2$; Me$_2$Si(4-oPh$_2$-2-nC$_6$-Ind)$_2$ZrCl$_2$; Me$_2$Si(4-oPh$_2$-2-nC$_5$-Ind)$_2$ZrCl$_2$; Me$_2$Si(4-oPh$_2$-2-nBu-Ind)$_2$ZrCl$_2$; Me$_2$Si(4-oPh$_2$-2-nC$_7$-Ind)$_2$ZrCl$_2$; Me$_2$Si(4-oPh$_2$-2-nC$_8$-Ind)$_2$ZrCl$_2$; Me$_2$Si(4-oPh$_2$-2-nC$_9$-Ind)$_2$ZrCl$_2$; Me$_2$Si(4-oPh$_2$-2-nC$_{10}$-Ind)$_2$ZrCl$_2$; Me$_2$Si(4-oPh$_2$-2-nBu-Ind)(4-(3', 5'-tBU$_2$-4'-OMePh)-2-Me-THI)ZrCl$_2$; Me$_2$Si(4-oPh$_2$-2-nC$_5$-Ind)(4-(3',5'-tBu$_2$-4'-OMePh)-2-Me-THI)ZrCl$_2$; Me$_2$Si(4-oPh$_2$-2-nC$_6$-Ind)(4-(3',5'-tBu$_2$-4'-OMePh)-2-Me-THI)ZrCl$_2$; Me$_2$Si(4-oPh$_2$-2-nC$_7$-Ind)(4-(3',5'-tBu$_2$-4'-OMePh)-2-Me-THI)ZrCl$_2$; Me$_2$Si(4-oPh$_2$-2-nC$_8$-Ind)(4-(3',5'-tBu$_2$-4'-OMePh)-2-Me-THI)ZrCl$_2$; Me$_2$Si(4-oPh$_2$-2-nC$_9$-Ind)(4-(3',5'-tBu$_2$-4'-OMePh)-2-Me-THI)ZrCl$_2$; Me$_2$Si(4-oPh$_2$-2-nC$_{10}$-Ind)(4-(3',5'-tBu$_2$-4'-OMePh)-2-Me-THI)ZrCl$_2$; Me$_2$Si(4-oPh$_2$-2-nBu-Ind)(4-(3',5'-tBu$_2$-4'-OMePh)-2-Me-THI)ZrCl$_2$; Me$_2$Si(4-oPh$_2$-2-nC$_5$-Ind)(4-(3',5'-tBu$_2$-4'-OMePh)-2-Me-THI)ZrCl$_2$; Me$_2$Si(4-oPh$_2$-2-nC$_6$-Ind)(4-(3',5'-tBu$_2$-4'-OMePh)-2-Me-THI)ZrCl$_2$; Me$_2$Si(4-oPh$_2$-2-nC$_7$-Ind)(4-(3',5'-tBu$_2$-4'-OMePh)-2-Me-THI)ZrCl$_2$; Me$_2$Si(4-oPh$_2$-2-nC$_8$-Ind)(4-(3',5'-tBu$_2$-4'-OMePh)-2-Me-THI)ZrCl$_2$; Me$_2$Si(4-oPh$_2$-2-nC$_9$-Ind)(4-(3',5'-tBu$_2$-4'-OMePh)-2-Me-THI)ZrCl$_2$; Me$_2$Si(4-oPh$_2$-2-nBu-Ind)(4-(3',5'-tBu$_2$)-2-Me-THI)ZrCl$_2$; Me$_2$Si(4-oPh$_2$-2-nC$_5$-Ind)(4-(3',5'-tBu$_2$)-2-Me-THI)ZrCl$_2$; Me$_2$Si(4-oPh$_2$-2-nC$_6$-Ind)(4-(3',5'-tBu$_2$)-2-Me-THI)ZrCl$_2$; Me$_2$Si(4-oPh$_2$-2-nC$_7$-Ind)(4-(3',5'-tBu$_2$)-2-Me-THI)ZrCl$_2$; Me$_2$Si(4-oPh$_2$-2-nC$_8$-Ind)(4-(3',5'-tBu$_2$)-2-Me-THI)ZrCl$_2$; Me$_2$Si(4-oPh$_2$-2-nC$_9$-Ind)(4-(3',5'-tBu$_2$)-2-Me-THI)ZrCl$_2$; Me$_2$Si(4-oPh$_2$-2-nC$_{10}$-Ind)(4-(3',5'-tBu$_2$)-2-Me-THI)ZrCl$_2$; Me$_2$Si(4-oPh$_2$-2-nBu-Ind)(4-(3',5'-tBu$_2$)-2-Me-THI)ZrCl$_2$; Me$_2$Si(4-oPh$_2$-2-nC$_5$-Ind)(4-(3',5'-tBu$_2$)-2-Me-THI)ZrCl$_2$; Me$_2$Si(4-oPh$_2$-2-nC$_6$-Ind)(4-(3',5'-tBu$_2$)-2-Me-THI)ZrCl$_2$; Me$_2$Si(4-oPh$_2$-2-nC$_7$-Ind)(4-(3',5'-tBu$_2$)-2-Me-THI)ZrCl$_2$; Me$_2$Si(4-oPh$_2$-2-nC$_8$-Ind)(4-(3',5'-tBu$_2$)-2-Me-THI)ZrCl$_2$; Me$_2$Si(4-oPh$_2$-2-nC$_9$-Ind)(4-(3',5'-tBu$_2$)-2-Me-THI)ZrCl$_2$; Me$_2$Si(4-oPh$_2$-2-nBu-Ind)(4-(3',5'-tBu$_2$-4'-OMePh)-2-t-THI)ZrCl$_2$; Me$_2$Si(4-oPh$_2$-2-nC$_5$-Ind)(4-(3', 5'-tBu$_2$-4'-OMePh)-2-t-THI)ZrCl$_2$; Me$_2$Si(4-oPh$_2$-2-nC$_6$-Ind)(4-(3',5'-tBu$_2$-4'-OMePh)-2-Et-THI)ZrCl$_2$; Me$_2$Si(4-oPh$_2$-2-nC$_7$-Ind)(4-(3',5'-tBu$_2$-4'-OMePh)-2-Et-THI)ZrCl$_2$; Me$_2$Si(4-oPh$_2$-2-nC$_8$-Ind)(4-(3',5'-tBu$_2$-4'-OMePh)-2-t-THI)ZrCl$_2$; Me$_2$Si(4-oPh$_2$-2-nC$_9$-Ind)(4-(3',5'-tBu$_2$-4'-OMePh)-2-t-THI)ZrCl$_2$; Me$_2$Si(4-oPh$_2$-2-nBu-Ind)(4-(3',5'-tBu$_2$-4'-OMePh)-2-n-propyl-THI)ZrCl$_2$; Me$_2$Si(4-oPh$_2$-2-nC$_5$-Ind)(4-(3',5'-tBu$_2$-4'-OMePh)-2-n-propyl-THI)ZrCl$_2$; Me$_2$Si(4-oPh$_2$-2-nC$_6$-Ind)(4-(3',5'-tBu$_2$-4'-OMePh)-2-n-propyl-THI)ZrCl$_2$; Me$_2$Si(4-oPh$_2$-2-nC$_7$-Ind)(4-(3',5'-tBu$_2$-4'-OMePh)-2-n-propyl-THI) ZrCl$_2$; Me$_2$Si(4-oPh$_2$-2-nC$_8$-Ind)(4-(3',5'-tBu$_2$-4'-OMePh)-2-n-propyl-THI)ZrCl$_2$; Me$_2$Si(4-oPh$_2$-2-nC$_9$-Ind)(4-(3',5'-tBu$_2$-4'-OMePh)-2-n-propyl-THI) ZrCl$_2$; Me$_2$Si(4-oPh$_2$-2-Me-Ind)(4-(3',5'-tBu$_2$-4'-OMePh)-2-nBu-THI) ZrCl$_2$; Me$_2$Si(4-oPh$_2$-2-Me-Ind)(4-(3',5'-tBu$_2$-4'-OMePh)-2-nC$_5$-THI)ZrCl$_2$; Me$_2$Si(4-oPh$_2$-2-Me-Ind)(4-(3',5'-tBu$_2$-4'-OMePh)-2-n-hexyl-THI) ZrCl$_2$; Me$_2$Si(4-oPh$_2$-2-Me-Ind)(4-(3',5'-tBu$_2$-4'-OMePh)-2-nC$_7$-THI)ZrCl$_2$; Me$_2$Si(4-oPh$_2$-2-Me-Ind)(4-(3',5'-tBu$_2$-4'-OMePh)-2-nC$_5$-THI)ZrCl$_2$; Me$_2$Si(4-oPh$_2$-2-Me-Ind)(4-(3', 5'-tBu$_2$-4'-OMePh)-2-nC$_9$-THI)ZrCl$_2$; Me$_2$Si(4-oPh$_2$-2-Me-Ind)(4-(3',5'-tBu$_2$-4'-OMePh)-2-nC$_{10}$-THI)ZrCl$_2$; Me$_2$Si(4-oPh$_2$-2-nBu-Ind)(4-(3',5'-tBu$_2$-4'-OMePh)-2-nBu-THI)ZrCl$_2$; Me$_2$Si(4-oPh$_2$-2-nC$_5$-Ind)(4-(3',5'-tBu$_2$-4'-OMePh)-2-nC$_5$-THI)ZrCl$_2$; Me$_2$Si(4-oPh$_2$-2-n-hexyl-Ind)(4-(3',5'-tBu$_2$-4'-OMePh)-2-n-hexyl-THI)ZrCl$_2$; Me$_2$Si(4-oPh$_2$-2-nBu-Ind)(4-(3',5'-tBu$_2$-4'-OMePh)-2-nC$_7$-THI)ZrCl$_2$; and Me$_2$Si(4-oPh$_2$-2-n-hexyl-Ind)(4-(3',5'-tBu$_2$-4'-OMePh)-2-nC$_8$-THI)ZrCl$_2$, where oPh$_2$ is o-biphenyl, nC$_6$ is n-hexyl, t-Bu$_2$ and tBu$_2$ are di-tertiary butyl, nBu is n-butyl, OMe is methoxy, Ind is indenyl, Ph is phenyl, nC$_3$ and nPr are n-propyl, oPh$_2$ is ortho-biphenyl, nC$_5$ is n-pentyl, nC$_7$ is n-heptyl, nC$_8$ is n-octyl, nC$_9$ is n-nonyl, nC$_{10}$ is n-decyl, Me is methyl, Et is ethyl, THI is 1,5,6,7-tetrahydro-s-indacenyl, and OMe-Ph and OMePh are methoxyphenyl. The hafnium analogs of the Zr compounds listed above are also useful as catalyst compounds herein.

Activators

The terms "cocatalyst" and "activator" are used herein interchangeably and are defined to be any compound which can activate any one of the catalyst compounds described above by converting the neutral catalyst compound to a catalytically active catalyst compound cation. Non-limiting activators, for example, include ionizing activators, which may be neutral or ionic, e.g. a non-coordinating anion. Preferred activators typically include ionizing anion precursor compounds that abstract a reactive, σ-bound, metal ligand making the metal complex cationic and providing a charge-balancing noncoordinating or weakly coordinating anion.

In embodiments, little or no alumoxane is used in the polymerization processes described herein. Preferably, alumoxane is present at zero mol %, alternately the alumoxane is present at a molar ratio of aluminum to catalyst compound transition metal less than 500:1, preferably less than 300:1, preferably less than 100:1, preferably less than 1:1.

The term "non-coordinating anion" (NCA) means an anion which either does not coordinate to a cation or which is only weakly coordinated to a cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient liability to permit displacement during polymerization.

It is within the scope of this invention to use an ionizing or stoichiometric activator, neutral or ionic, such as tri (n-butyl) ammonium tetrakis (pentafluorophenyl) borate, a tris perfluorophenyl boron metalloid precursor or a tris perfluoronaphthyl boron metalloid precursor, polyhalogenated heteroborane anions (WO 98/43983), boric acid (U.S. Pat. No. 5,942,459), or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium, and indium, or mixtures thereof. The three substituent groups are each independently selected from alkyls, alkenyls, halogens, substituted alkyls, aryls, arylhalides, alkoxy, and halides. Preferably, the three groups are independently selected from halogen, mono or multicyclic (including halosubstituted) aryls, alkyls, and alkenyl compounds, and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl, or mixtures thereof. Even more preferably, the three groups are halogenated, preferably fluorinated, aryl groups. A preferred neutral stoichiometric activator is tris perfluorophenyl boron or tris perfluoronaphthyl boron.

Ionic stoichiometric activator compounds may contain an active proton, or some other cation associated with, but not coordinated to, or only loosely coordinated to, the remaining ion of the ionizing compound. Such compounds, and the like, are described in European publications EP 0 570 982 A; EP 0 520 732 A; EP 0 495 375 A; EP 0 500 944 B1; EP 0 277 003 A; EP 0 277 004 A; U.S. Pat. Nos. 5,153,157; 5,198,401; 5,066,741; 5,206,197; 5,241,025; 5,384,299; 5,502,124; and U.S. Ser. No. 08/285,380, filed Aug. 3, 1994; all of which are herein fully incorporated by reference.

Preferred compounds useful as an activator in the process of this invention comprise a cation, which is preferably a Bronsted acid capable of donating a proton, and a compatible non-coordinating anion which anion is relatively large (bulky), capable of stabilizing the active catalyst species (the Group 4 cation) which is formed when the two compounds are combined and said anion will be sufficiently labile to be displaced by olefinic, diolefinic and acetylenically unsaturated substrates or other neutral Lewis bases, such as ethers, amines, and the like. Two classes of useful compatible non-coordinating anions have been disclosed in EP 0 277, 003 A1, and EP 0 277,004 A1: 1) anionic coordination complexes comprising a plurality of lipophilic radicals covalently coordinated to and shielding a central charge-bearing metal or metalloid core; and 2) anions comprising a plurality of boron atoms such as carboranes, metallacarboranes, and boranes.

In a preferred embodiment, the stoichiometric activators include a cation and an anion component, and are preferably represented by the following formula (II):

$$(Z)_d^+(A^{d-}) \qquad (II)$$

wherein Z is (L-H) or a reducible Lewis Acid, L is an neutral Lewis base; H is hydrogen; (L-H)$^+$ is a Bronsted acid; $A^{d-}$ is a non-coordinating anion having the charge d−; and d is an integer from 1 to 3.

When Z is (L-H) such that the cation component is $(L-H)_d^+$, the cation component may include Bronsted acids such as protonated Lewis bases capable of protonating a moiety, such as an alkyl or aryl, from the bulky ligand metallocene containing transition metal catalyst precursor, resulting in a cationic transition metal species. Preferably, the activating cation $(L-H)_d^+$ is a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether diethyl ether, tetrahydrofuran, and dioxane, sulfoniums from thioethers, such as diethyl thioethers and tetrahydrothiophene, and mixtures thereof.

When Z is a reducible Lewis acid it is preferably represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl, preferably the reducible Lewis acid is represented by the formula: $(Ph_3C^+)$, where Ph is phenyl or phenyl substituted with a heteroatom, a $C_1$ to $C_{40}$ hydrocarbyl, or a substituted $C_1$ to $C_{40}$ hydrocarbyl. In a preferred embodiment, the reducible Lewis acid is triphenyl carbenium.

The anion component $A^{d-}$ include those having the formula $[M^{k+}Q_n]^{d-}$ wherein k is 1, 2, or 3; n is 1, 2, 3, 4, 5, or 6; n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide, and two Q groups may form a ring structure. Preferably, each Q is a fluorinated hydrocarbyl group having 1 to 20 carbon atoms, more preferably each Q is a fluorinated aryl group, and most preferably each Q is a pentafluoryl aryl group.

Examples of suitable $A^{d-}$ components also include diboron compounds as disclosed in U.S. Pat. No. 5,447,895, which is fully incorporated herein by reference.

In a preferred embodiment, this invention relates to a method to polymerize olefins comprising contacting olefins (preferably ethylene) with a catalyst compound and a boron containing NCA activator represented by the formula (14):

$$Z_d^+(A^{d-}) \qquad (14)$$

where: Z is (L-H) or a reducible Lewis acid; L is an neutral Lewis base (as further described above); H is hydrogen; (L-H) is a Bronsted acid (as further described above); $A^{d-}$ is a boron containing non-coordinating anion having the charge d− (as further described above); d is 1, 2, or 3.

In a preferred embodiment in any NCA represented by Formula 14 described above, the reducible Lewis acid is represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl, preferably the reducible Lewis acid is represented by the formula: $(Ph_3C^+)$, where Ph is phenyl or phenyl substituted with a heteroatom, a $C_1$ to $C_{40}$ hydrocarbyl, or a substituted $C_1$ to $C_{40}$ hydrocarbyl.

In a preferred embodiment in any of the NCAs represented by Formula 14 described above, $Z_d^+$ is represented by the formula: $(L-H)_d^+$, wherein L is an neutral Lewis base; H is hydrogen; (L-H) is a Bronsted acid; and d is 1, 2, or 3, preferably $(L-H)_d^+$ is a Bronsted acid selected from ammoniums, oxoniums, phosphoniums, silyliums, and mixtures thereof.

In a preferred embodiment in any of the NCAs represented by Formula 14 described above, the anion component $A^{d-}$ is represented by the formula $[M^{*k^*+}Q^*_{n^*}]^{d^*-}$ wherein k* is 1, 2, or 3; n* is 1, 2, 3, 4, 5, or 6 (preferably 1, 2, 3, or 4); n*−k*=d*; M* is boron; and Q* is independently selected from hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q* having up to 20 carbon atoms with the proviso that in not more than 1 occurrence is Q* a halide.

This invention also relates to a method to polymerize olefins comprising contacting olefins (such as ethylene) with a catalyst compound and an NCA activator represented by the formula (I):

$$R_nM^{**}(ArNHal)_{4-n} \qquad (I)$$

where R is a monoanionic ligand; M** is a Group 13 metal or metalloid; ArNHal is a halogenated, nitrogen-containing aromatic ring, polycyclic aromatic ring, or aromatic ring assembly in which two or more rings (or fused ring systems) are joined directly to one another or together; and n is 0, 1, 2, or 3. Typically the NCA comprising an anion of Formula I also comprises a suitable cation that is essentially non-interfering with the ionic catalyst complexes formed with the transition metal compounds, preferably the cation is $Z_d^+$ as described above.

In a preferred embodiment in any of the NCAs comprising an anion represented by Formula I described above, R is selected from the group consisting of substituted or unsubstituted $C_1$ to $C_{30}$ hydrocarbyl aliphatic or aromatic groups, where substituted means that at least one hydrogen on a carbon atom is replaced with a hydrocarbyl, halide, halocarbyl, hydrocarbyl or halocarbyl substituted organometalloid, dialkylamido, alkoxy, aryloxy, alkysulfido, arylsulfido, alkylphosphido, arylphosphide, or other anionic substituent; fluoride; bulky alkoxides, where bulky means $C_4$ to $C_{20}$ hydrocarbyl groups; $—SR^1$, $—NR^2_2$, and $—PR^3_2$, where each $R^1$, $R^2$, or $R^3$ is independently a substituted or unsubstituted hydrocarbyl as defined above; or a $C_1$ to $C_{30}$ hydrocarbyl substituted organometalloid.

In a preferred embodiment in any of the NCAs comprising an anion represented by Formula I described above, the NCA also comprises cation comprising a reducible Lewis acid represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl, preferably the reducible Lewis acid represented by the formula: $(Ph_3C^+)$, where Ph is phenyl or phenyl substituted with a heteroatom, a $C_1$ to $C_{40}$ hydrocarbyl, or a substituted $C_1$ to $C_{40}$ hydrocarbyl.

In a preferred embodiment in any of the NCAs comprising an anion represented by Formula I described above, the NCA also comprises a cation represented by the formula, $(L-H)_d^+$, wherein L is an neutral Lewis base; H is hydrogen; (L-H) is a Bronsted acid; and d is 1, 2, or 3, preferably $(L-H)_d^+$ is a Bronsted acid selected from ammoniums, oxoniums, phosphoniums, silyliums, and mixtures thereof.

Further examples of useful activators include those disclosed in U.S. Pat. Nos. 7,297,653 and 7,799,879.

Another activator useful herein comprises a salt of a cationic oxidizing agent and a noncoordinating, compatible anion represented by the formula (16):

$$(OX^{e+})_d(A^{d-})_e \qquad (16)$$

wherein $OX^{e+}$ is a cationic oxidizing agent having a charge of e+; e is 1, 2, or 3; d is 1, 2 or 3; and $A^{d-}$ is a non-coordinating anion having the charge of d− (as further described above).

Examples of cationic oxidizing agents include: ferrocenium, hydrocarbyl-substituted ferrocenium, $Ag^+$, or $Pb^{+2}$. Preferred embodiments of $A^{d-}$ include tetrakis(pentafluorophenyl)borate.

In another embodiment, the catalyst compounds described herein can be used with Bulky activators. A "Bulky activator" as used herein refers to anionic activators represented by the formula:

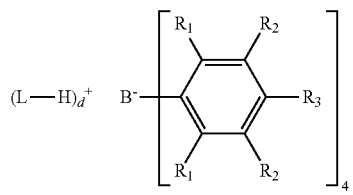

where:
each $R_1$ is, independently, a halide, preferably a fluoride;
each $R_2$ is, independently, a halide, a $C_6$ to $C_{20}$ substituted aromatic hydrocarbyl group or a siloxy group of the formula $—O—Si—R_a$, where $R_a$ is a $C_1$ to $C_{20}$ hydrocarbyl or hydrocarbylsilyl group (preferably $R_2$ is a fluoride or a perfluorinated phenyl group);

each $R_3$ is a halide, $C_6$ to $C_{20}$ substituted aromatic hydrocarbyl group or a siloxy group of the formula $—O—Si—R_a$, where $R_a$ is a $C_1$ to $C_{20}$ hydrocarbyl or hydrocarbylsilyl group (preferably $R_3$ is a fluoride or a $C_6$ perfluorinated aromatic hydrocarbyl group); wherein $R_2$ and $R_3$ can form one or more saturated or unsaturated, substituted or unsubstituted rings (preferably $R_2$ and $R_3$ form a perfluorinated phenyl ring);

L is an neutral Lewis base; $(L-H)^+$ is a Bronsted acid; d is 1, 2, or 3;

wherein the anion has a molecular weight of greater than 1020 g/mol; and wherein at least three of the substituents on the B atom each have a molecular volume of greater than 250 cubic Å, alternately greater than 300 cubic Å, or alternately greater than 500 cubic Å.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple "Back of the Envelope" Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: $MV=8.3V_s$, where $V_s$ is the scaled volume. $V_s$ is the sum of the relative volumes of the constituent atoms, and is calculated from the molecular formula of the substituent using the following table of relative volumes. For fused rings, the $V_s$ is decreased by 7.5% per fused ring.

| Element | Relative Volume |
|---|---|
| H | 1 |
| $1^{st}$ short period, Li to F | 2 |
| $2^{nd}$ short period, Na to Cl | 4 |
| $1^{st}$ long period, K to Br | 5 |
| $2^{nd}$ long period, Rb to I | 7.5 |
| $3^{rd}$ long period, Cs to Bi | 9 |

Exemplary bulky substituents of activators suitable herein and their respective scaled volumes and molecular volumes are shown in the table at column 20, line 35 et seq. of U.S. Pat. No. 9,266,977.

For a list of particularly useful Bulky activators please see U.S. Pat. No. 8,658,556, which is incorporated by reference herein.

In another embodiment, one or more of the NCA activators is chosen from the activators described in U.S. Pat. No. 6,211,105.

Preferred activators include N,N-dimethylanilinium tetrakis(perfluoronaphthalen-2-yl)borate, N,N-dimethylanilinium tetrakis(perfluorobiphenyl)borate, N,N-dimethylanilinium tetrakis(perfluorophenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, $[Me_3NH^+][B(C_6F_5)_4^-]$; 1-(4-(tris (pentafluorophenyl)borate)-2,3,5,6-tetrafluorophenyl) pyrrolidinium; and 4-(tris(pentafluorophenyl)borate)-2,3,5,6-tetrafluoropyridine.

In a preferred embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl) borate, triphenylcarbenium tetrakis(perfluoronaphthyl) borate, triphenylcarbenium tetrakis(perfluorobiphenyl) borate, triphenylcarbenium tetrakis(3,5-bis(trifluoromethyl) phenyl)borate).

In another embodiment, the activator comprises one or more of trialkylammonium tetrakis(pentafluorophenyl)borate, N,N-dialkylanilinium tetrakis(pentafluorophenyl)borate, N,N-dimethyl-(2,4,6-trimethylanilinium) tetrakis(pentafluorophenyl)borate, trialkylammonium tetrakis-(2,3,4,6-tetrafluorophenyl) borate, N,N-dialkylanilinium tetrakis-(2,3,4,6-tetrafluorophenyl)borate, trialkylammonium tetrakis(perfluoronaphthyl)borate, N,N-dialkylanilinium tetrakis(perfluoronaphthyl)borate, trialkylammonium tetrakis(perfluorobiphenyl)borate, N,N-dialkylanilinium tetrakis(perfluorobiphenyl)borate, trialkylammonium tetrakis(3,5-bis(trifluoromethyl)phenyl)borate, N,N-dialkylanilinium tetrakis(3,5-bis(trifluoromethyl)phenyl)borate, N,N-dialkyl-(2,4,6-trimethylanilinium) tetrakis(3,5-bis(trifluoromethyl) phenyl)borate, di-(i-propyl)ammonium tetrakis(pentafluorophenyl)borate, (where alkyl is methyl, ethyl, propyl, n-butyl, sec-butyl, or t-butyl).

In a preferred embodiment, any of the activators described herein may be mixed together before or after combination with the catalyst compound, preferably before being mixed with the catalyst compound.

In some embodiments two NCA activators may be used in the polymerization and the molar ratio of the first NCA activator to the second NCA activator can be any ratio. In some embodiments, the molar ratio of the first NCA activator to the second NCA activator is 0.01:1 to 10,000:1, preferably 0.1:1 to 1000:1, preferably 1:1 to 100:1.

Further, the typical activator-to-catalyst ratio, e.g., all NCA activators-to-catalyst ratio is a 1:1 molar ratio. Alternate preferred ranges include from 0.1:1 to 100:1, alternately from 0.5:1 to 200:1, alternately from 1:1 to 500:1, alternately from 1:1 to 1000:1. A particularly useful range is from 0.5:1 to 10:1, preferably 1:1 to 5:1.

It is also within the scope of this invention that the catalyst compounds can be combined with combinations of alumoxanes and NCAs (see, for example, U.S. Pat. Nos. 5,153,157; 5,453,410; EP 0 573 120 B1; WO 94/07928; and WO 95/14044 which discuss the use of an alumoxane in combination with an ionizing activator).

Optional Scavengers or Co-Activators

In addition to these activator compounds, scavengers or co-activators may be used. Aluminum alkyl or organoaluminum compounds which may be utilized as scavengers or co-activators include, for example, trimethylaluminum, triethylaluminum, triisobutylaluminum, tri-n-hexylaluminum, tri-n-octylaluminum, and diethyl zinc.

Chain Transfer Agents

This invention further relates to methods to polymerize olefins using the above catalysts in the presence of a chain transfer agent that may be hydrogen or a main-group metal organometallic compound.

A "chain transfer agent" is any agent capable of hydrocarbyl and/or polymeryl group exchange between a coordinative polymerization catalyst and the chain transfer agent during a polymerization process. The chain transfer agent can be any desirable chemical compound such as those disclosed in WO 2007/130306. Preferably, the chain transfer agent is selected from Group 2, 12, or 13 alkyl or aryl compounds; preferably zinc, magnesium or aluminum alkyls or aryls; preferably where the alkyl is a $C_1$ to $C_{30}$ alkyl, alternately a $C_2$ to $C_{20}$ alkyl, alternately a $C_3$ to $C_{12}$ alkyl, typically selected independently from methyl, ethyl, propyl, butyl, isobutyl, tertbutyl, pentyl, hexyl, cyclohexyl, phenyl, octyl, nonyl, decyl, undecyl, and dodecyl; and where diethylzinc is particularly preferred.

In a particularly useful embodiment, this invention relates to a catalyst system comprising activator, catalyst compound as described herein and chain transfer agent wherein the chain transfer agent is selected from Group 2, 12, or 13 alkyl or aryl compounds.

In a particularly useful embodiment, the chain transfer agent is selected from dialkyl zinc compounds, where the alkyl is selected independently from methyl, ethyl, propyl, butyl, isobutyl, tertbutyl, pentyl, hexyl, cyclohexyl, and phenyl.

In a particularly useful embodiment, the chain transfer agent is selected from trialkyl aluminum compounds, where the alkyl is selected independently from methyl, ethyl, propyl, butyl, isobutyl, tertbutyl, pentyl, hexyl, cyclohexyl, and phenyl.

Useful chain transfer agents are typically present at from 10 or 20 or 50 or 100 equivalents to 600 or 700 or 800 or 1000 equivalents relative to the catalyst component. Alternately the chain transfer agent ("CTA") is preset at a catalyst complex-to-CTA molar ratio of from about 1:3000 to 10:1; alternatively about 1:2000 to 10:1; alternatively about 1:1000 to 10:1; alternatively about 1:500 to 1:1; alternatively about 1:300 to 1:1; alternatively about 1:200 to 1:1; alternatively about 1:100 to 1:1; alternatively about 1:50 to 1:1; alternatively about 1:10 to 1:1.

Useful chain transfer agents include diethylzinc, tri-n-octyl aluminum, trimethylaluminum, triethylaluminum, triisobutylaluminum, tri-n-hexylaluminum, diethyl aluminum chloride, dibutyl zinc, di-n-propylzinc, di-n-hexylzinc, di-n-pentylzinc, di-n-decylzinc, di-n-dodecylzinc, di-n-tetradecylzinc, di-n-hexadecylzinc, di-n-octadecylzinc, diphenylzinc, diisobutylaluminum hydride, diethylaluminum hydride, di-n-octylaluminum hydride, dibutylmagnesium, diethylmagnesium, dihexylmagnesium, and triethylboron.

Polymerization Processes

In embodiments herein, the invention relates to polymerization processes where monomer (such as propylene), and optionally comonomer, are contacted with a catalyst system comprising a non-coordinating anion activator and at least one metallocene compound, as described above. The catalyst compound and activator may be combined in any order, and are combined typically prior to contacting with the monomer.

Monomers useful herein include substituted or unsubstituted $C_2$ to $C_{40}$ alpha olefins, preferably $C_2$ to $C_{20}$ alpha olefins, preferably $C_2$ to $C_{12}$ alpha olefins, preferably ethylene, propylene, butene, pentene, hexene, heptene, octene, nonene, decene, undecene, dodecene and isomers thereof. In a preferred embodiment of the invention, the monomer comprises propylene and an optional comonomers comprising one or more of ethylene or $C_4$ to $C_{40}$ olefins, preferably $C_4$ to $C_{20}$ olefins, or preferably $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups. In another preferred embodiment, the monomer comprises ethylene and an optional comonomer comprising one or more $C_3$ to $C_{40}$ olefins, preferably $C_4$ to $C_{20}$ olefins, or preferably $C_6$ to $C_{12}$ olefins. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Exemplary $C_2$ to $C_{40}$ olefin monomers and optional comonomers include ethylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, preferably hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, preferably norbornene, norbornadiene, and dicyclopentadiene.

Polymerization processes of this invention can be carried out in any manner known in the art. Any homogeneous, bulk, solution (including supercritical) phase polymerization process known in the art can be used. Such processes can be run in a batch, semi-batch, or continuous mode. Homogeneous polymerization processes and slurry processes are preferred. (A homogeneous polymerization process is defined to be a process where at least 90 wt % of the product is soluble in the reaction media.) A bulk homogeneous process is particularly preferred. (A bulk process is typically a process where monomer concentration in all feeds to the reactor is 70 vol % or more.) Alternately, no solvent or diluent is present or added in the reaction medium, (except for the small amounts used as the carrier for the catalyst system or other additives, or amounts typically found with the monomer; e.g., propane in propylene).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_{4-10}$ alkanes, chlorobenzene, and aromatic and alkylsubstituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably less than 0.5 wt %, preferably less than 0 wt % based upon the weight of the solvents.

In a preferred embodiment, the feed concentration of the monomers and comonomers for the polymerization is 60 vol % solvent or less, preferably 40 vol % or less, or preferably 20 vol % or less, based on the total volume of the feedstream. Preferably, the polymerization is run in a bulk process.

Preferred polymerizations can be run at any temperature and/or pressure suitable to obtain the desired polymers. Typical temperatures and/or pressures include a temperature in the range of from about 80° C. to about 300° C., preferably from about 85° C. to about 200° C., preferably from about 90° C. to about 150° C., preferably from about 90° C. to about 120° C., preferably from about 95° C. to about 110° C.; and at a pressure in the range of from about 0.35 MPa to about 10 MPa, preferably from about 0.45 MPa to about 6 MPa, or preferably from about 0.5 MPa to about 4 MPa.

In a typical polymerization, the ethylene is present in the polymerization reactor at a partial pressure of 0 to 1000 psig (0 to 6900 kPa), 5 to 300 psig (34 to 2068 kPa), more preferably 10 to 100 psig (69 to 690 kPa).

In a typical polymerization, the run time of the reaction is up to 300 minutes, preferably in the range of from about 5 to 250 minutes, or preferably from about 10 to 120 minutes.

In another embodiment of the invention, the polymerization temperature is preferably from about 70° C. to about 130° C., preferably from about 80° C. to about 125° C., preferably from about 90° C. to about 120° C., preferably from about 95° C. to about 110° C. and the polymerization process is a homogeneous process, preferably a solution process.

In some embodiments, hydrogen is present in the polymerization reactor at a partial pressure of 0.001 to 50 psig (0.007 to 345 kPa), preferably from 0.01 to 25 psig (0.07 to 172 kPa), more preferably from 0.1 to 10 psig (0.7 to 70 kPa). In some embodiments, hydrogen is not added the polymerization reactor, i.e., hydrogen may be present from other sources, such as a hydrogen generating catalyst, but none is added to the reactor.

In an embodiment of the invention, the activity of the catalyst is at least 50 g/mmol/hour, preferably 500 g/mmol/hour or more, preferably 5000 g/mmol/hr or more, preferably 50,000 g/mmol/hr or more, preferably 100,000 g/mmol/hr or more, preferably 150,000 g/mmol/hr or more, preferably 200,000 g/mmol/hr or more, preferably 250,000 g/mmol/hr or more, preferably 300,000 g/mmol/hr or more, preferably 350,000 g/mmol/hr or more. In an alternate embodiment, the conversion of olefin monomer is at least 10%, based upon polymer yield and the weight of the monomer entering the reaction zone, preferably 20% or more, preferably 30% or more, preferably 50% or more, preferably 80% or more.

In a preferred embodiment, little or no scavenger is used in the process to produce the ethylene polymer. Preferably, scavenger (such as tri alkyl aluminum) is present at zero mol %, alternately the scavenger is present at a molar ratio of scavenger metal to transition metal of less than 100:1, preferably less than 50:1, preferably less than 15:1, preferably less than 10:1.

In a preferred embodiment, the polymerization: 1) is conducted at temperatures of 80° C. to 130° C. (preferably 90° C. to 120° C., preferably 95° C. to 120° C.); 2) is conducted at a pressure of atmospheric pressure to 10 MPa (preferably from 0.35 to 10 MPa, preferably from 0.45 to 6 MPa, preferably from 0.5 to 4 MPa); 3) is conducted in an aliphatic hydrocarbon solvent (such as, isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof; preferably where aromatics are preferably present in the solvent at less than 1 wt %, preferably less than 0.5 wt %, preferably at 0 wt % based upon the weight of the solvents); 4) ethylene is present in the polymerization reactor at a partial pressure of 0 to 1000 psig (0 to 6900 kPa), preferably 5 to 300 psig (34 to 2068 kPa), more preferably 10 to 100 psig (69 to 690 kPa); 5) the polymerization preferably occurs in one reaction zone; 6) the productivity of the catalyst compound is at least 80,000 g/mmol/hr (preferably at least 150,000 g/mmol/hr, preferably at least 200,000 g/mmol/hr, preferably at least 250,000 g/mmol/hr, preferably at least 300,000 g/mmol/hr); 7) optionally, scavengers (such as trialkyl aluminum compounds) are absent (e.g., present at zero mol %, alternately the scavenger is present at a molar ratio of scavenger metal to transition metal of less than 100:1, preferably less than 50:1, preferably less than 15:1, preferably less than 10:1); and 8) optionally, hydrogen is present in the polymerization reactor at a partial pressure of 0.001 to 50 psig (0.007 to 345 kPa) (preferably from 0.01 to 25 psig (0.07 to 172 kPa), more preferably 0.1 to 10 psig (0.7 to 70 kPa)).

In a preferred embodiment, the catalyst system used in the polymerization comprises no more than one catalyst compound. A "reaction zone" also referred to as a "polymerization zone" is a vessel where polymerization takes place, for example a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In a preferred embodiment, the polymerization occurs in one reaction zone. Room temperature is 23° C. unless otherwise noted.

Other additives may also be used in the polymerization, as desired, such as one or more scavengers, promoters, modifiers, chain transfer agents (such as diethyl zinc or hydrogen), reducing agents, oxidizing agents, hydrogen, aluminum alkyls, or silanes.

Solution Phase Polymerization

As used herein, the phrase "solution phase polymerization" refers to a polymerization system where the polymer produced is soluble in the polymerization medium. Generally this involves polymerization in a continuous reactor in which the polymer formed and the starting monomer and catalyst materials supplied, are agitated to reduce or avoid concentration gradients and in which the monomer acts as a diluent or solvent or in which a hydrocarbon is used as a diluent or solvent. Suitable processes typically operate at temperatures from about 80° C. to about 250° C., preferably from about 80° C. to about 200° C., preferably from about 80° C. to about 150° C., more preferably from about 90° C. to about 140° C., more preferably from about 95° C. to about 120° C. and at pressures of about 0.1 MPa or more, preferably 2 MPa or more. The upper pressure limit is not critically constrained but typically can be about 200 MPa or less, preferably 120 MPa or less. Temperature control in the reactor can generally be obtained by balancing the heat of polymerization and with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds can also be used. The purity, type, and amount of solvent can be optimized for the maximum catalyst productivity for a particular type of polymerization. The solvent can be also introduced as a catalyst carrier. The solvent can be introduced as a gas phase or as a liquid phase depending on the pressure and temperature. Advantageously, the solvent can be kept in the liquid phase and introduced as a liquid. Solvent can be introduced in the feed to the polymerization reactors.

In a preferred embodiment, the polymerization process can be described as a continuous, non-batch process that, in its steady state operation, is exemplified by removal of amounts of polymer made per unit time, being substantially equal to the amount of polymer withdrawn from the reaction vessel per unit time. By "substantially equal" we intend that these amounts, polymer made per unit time, and polymer withdrawn per unit time, are in ratios of one to other, of from 0.9:1; or 0.95:1; or 0.97:1; or 1:1. In such a reactor, there will be a substantially homogeneous monomer distribution.

Preferably, in a continuous process, the mean residence time of the catalyst and polymer in the reactor generally can be from about 5 minutes to about 8 hours, and preferably from about 10 minutes to about 6 hours, more preferably from 10 minutes to 1 hour. In some embodiments, comonomer (such as ethylene) can be added to the reaction vessel in an amount to maintain a differential pressure in excess of the combined vapor pressure of the main monomer (such as a propylene) and any optional diene monomers present.

In another embodiment, the polymerization process can be carried out at a pressure of ethylene of from about 0 kPa to about 6900 kPa, preferably from about 34 to about 2068 kPa, most preferably from about 69 to 690 kPa. The polymerization is generally conducted at a temperature of from about 25° C. to about 250° C., preferably from about 75° C. to about 200° C., and most preferably from about 95° C. to about 200° C.

The addition of a small amount of hydrocarbon to a typical solution phase process can cause the polymer solution viscosity to drop and or the amount of polymer solute to increase. Addition of a larger amount of solvent in a traditional solution process can cause the separation of the polymer into a separate phase (which can be solid or liquid, depending on the reaction conditions, such as temperature or pressure).

The processes discussed and described herein can be carried out in continuous stirred tank reactors, batch reactors, or plug flow reactors. One reactor can be used even if sequential polymerizations are being performed, preferably as long as there is separation in time or space of the two reactions. Likewise, two or more reactors, operating in series or parallel, can also be used. These reactors can have, or not have, internal cooling and the monomer feed may or may not be refrigerated. See the general disclosure of U.S. Pat. No. 5,001,205 for general process conditions. See also, WO 96/33227 and WO 97/22639.

Supercritical or Supersolution Polymerization

In aspects of the invention, the processes and/or catalyst compositions disclosed herein may be used in a supercritical or super solution phase. A supercritical polymerization means a polymerization process in which the polymerization system is in a dense fluid (i.e., its density is 300 kg/m$^3$ or higher), supercritical state. The terms "dense fluid" and "supercritical state" are defined in U.S. Pat. No. 7,812,104. A super solution polymerization is one where the polymerization occurs at a temperature of 65° C. to 150° C., preferably from about 75° C. to about 140° C., preferably from about 90° C. to about 140° C., more preferably from about 100° C. to about 140° C., and at pressures of between 1.72 MPa and 35 MPa, preferably between 5 and 30 MPa. For further information on supercritical and super solution polymerizations, please see U.S. Pat. Nos. 7,812,104; 8,008,412; 7,812,104; 9,249,239; 7,729,536; 8,058,371; and US 2008/0153997.

Polyolefin Products

This invention also relates to compositions of matter produced by the methods described herein.

In a preferred embodiment, the process described herein produces propylene homopolymers or propylene copolymers, such as propylene-ethylene and/or propylene-alphaolefin (preferably $C_3$ to $C_{20}$) copolymers (such as propylene-hexene copolymers or propylene-octene copolymers), preferably having: an Mw/Mn of greater than 1 to 6 (preferably greater than 2 to 4).

Likewise, the process of this invention produces olefin polymers, preferably polypropylene homopolymers and copolymers. In a preferred embodiment, the polymers produced herein are homopolymers of propylene, are copolymers of propylene preferably having from 0 to 50 mol % (alternately from 0.5 to 25 mol %, alternately from 0.5 to 20 mol %, alternately from 1 to 15 mol %, preferably from 3 to 10 mol %) of one or more of ethylene or $C_4$ to $C_{20}$ olefin comonomer (preferably ethylene or $C_4$ to $C_{12}$ alpha-olefin, preferably ethylene, butene, hexene, octene, decene, dodecene, preferably propylene, butene, hexene, octene), or are copolymers of propylene preferably having from 0 to 25 mol % (alternately from 0.5 to 20 mol %, alternately from 1 to 15 mol %, preferably from 3 to 10 mol %) of one or more of $C_2$ or $C_4$ to $C_{20}$ olefin comonomer (preferably ethylene or $C_4$ to $C_{12}$ alpha-olefin, preferably ethylene, butene, hexene, octene, decene, dodecene, preferably ethylene, butene, hexene, octene).

In a preferred embodiment, the monomer is propylene and the comonomer is hexene, preferably from 1 to 15 mol % hexene, alternately 1 to 10 mol %.

In a preferred embodiment, the monomer is propylene and the comonomer is ethylene, preferably from 0.5 to 99.5 wt % ethylene, alternately from 1 to 65 wt % ethylene, alternately from 1 to 60 wt % ethylene, alternately from 2 to 50 wt % ethylene, alternately from 3 to 30 wt % ethylene, alternately from 4 to 20 wt % ethylene, based upon the weight of the copolymer.

Typically, the polymers produced herein have an Mw (as measured by GPC-DRI) from 5,000 to 1,000,000 g/mol, alternately from 200,000 to 1,000,000 g/mol, alternately 250,000 to 800,000 g/mol, alternately 300,000 to 600,000 g/mol, alternately from 300,000 to 500,000 g/mol.

Typically, the polymers produced herein have an Mw/Mn (as measured by GPC-DRI) of greater than 1 to 40, preferably 1 to 20, preferably 1.1 to 15, preferably 1.2 to 10, preferably 1.3 to 5, preferably 1.4 to 4.

Typically, the polymers produced herein have an Mw (as measured by GPC-DRI) of 5,000 to 1,000,000 g/mol (preferably 50,000 to 500,000 g/mol, preferably 100,000 to 400,000 g/mol, preferably 150,000 to 350,000 g/mol, preferably 200,000 to 300,000 g/mol) and/or an Mw/Mn of greater than 1 to 40 (alternately 1.5 to 20, alternately 1.8 to 10, alternately 2 to 5, 2 to 4, alternately 2 to 3).

In a preferred embodiment, the polymer produced herein has a unimodal or multimodal molecular weight distribution as determined by Gel Permeation Chromatography (GPC). By "unimodal" is meant that the GPC trace has one peak or three inflection points. By "multimodal" is meant that the GPC trace has at least two peaks or more than three inflection points. An inflection point is that point where the second derivative of the curve changes in sign (e.g., from negative to positive or vice versus).

The polymer produced herein can have a melting point (Tm, DSC peak second melt) of at least 145° C., or at least 150° C., or at least 152° C., or at least 153° C., or at least 154° C. For example, the polymer can have a melting point from at least 145° C. to about 175° C., about 150° C. to about 165° C., about 152° C. to about 160° C.

The polymer produced herein can have a 1% secant flexural modulus from a low of about 1100 MPa, about 1200 MPa, about 1250 MPa, about 1300 MPa, about 1400 MPa, or about 1,500 MPa to a high of about 1,800 MPa, about 2,100 MPa, about 2,600 MPa, or about 3,000 MPa, as measured according to ASTM D 790 (A, 1.0 mm/min). For example, the polymer can have a flexural modulus from about 1100 MPa to about 2,200 MPa, about 1200 MPa to about 2,000 MPa, about 1400 MPa to about 2,000 MPa, or about 1500 MPa or more, as measured according to ASTM D 790 (A, 1.0 mm/min).

The polymer produced herein can have a melt flow rate (MFR, ASTM 1238, 2.16 kg, 230° C.) from a low of about 0.1 dg/min, about 0.2 dg/min, about 0.5 dg/min, about 1 dg/min, about 15 dg/min, about 30 dg/min, or about 45 dg/min to a high of about 75 dg/min, about 100 dg/min, about 200 dg/min, or about 300 dg/min.

The polymer produced herein can have a branching index (g'vis) of 0.95 or less, preferably 0.93 or less, preferably 0.90 or less, preferably 0.88 or less.

Blends

In another embodiment, the polymer (preferably the polyethylene or polypropylene) produced herein is combined with one or more additional polymers prior to being formed into a film, molded part or other article. Other useful polymers include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In a preferred embodiment, the polymer produced herein is present in the above blends, at from 10 to 99 wt %, based upon the weight of the polymers in the blend, preferably 20 to 95 wt %, even more preferably at least 30 to 90 wt %, even more preferably at least 40 to 90 wt %, even more preferably at least 50 to 90 wt %, even more preferably at least 60 to 90 wt %, even more preferably at least 70 to 90 wt %.

The blends described above may be produced by mixing the polymers of the invention with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX™ 1010 or IRGANOX™ 1076 available from Ciba-Geigy); phosphites (e.g., IRGAFOS™ 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; and the like.

Films

Specifically, any of the foregoing polymers, such as the foregoing propylene polymers or blends thereof, may be used in a variety of end-use applications. Such applications include, for example, mono- or multi-layer blown, extruded, and/or shrink films. These films may be formed by any number of well-known extrusion or coextrusion techniques, such as a blown bubble film processing technique, wherein the composition can be extruded in a molten state through an annular die and then expanded to form a uni-axial or biaxial orientation melt prior to being cooled to form a tubular, blown film, which can then be axially slit and unfolded to form a flat film. Films may be subsequently unoriented, uniaxially oriented, or biaxially oriented to the same or different extents. One or more of the layers of the film may be oriented in the transverse and/or longitudinal directions to the same or different extents. The uniaxially orientation can be accomplished using typical cold drawing or hot drawing methods. Biaxial orientation can be accomplished using tenter frame equipment or a double bubble processes and may occur before or after the individual layers are brought together. For example, a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then optionally the combination could be oriented even further. Typically the films are oriented in the Machine Direction (MD) at a ratio of up to 15, preferably between 5 and 7, and in the Transverse Direction (TD) at a ratio of up to 15, preferably 7 to 9. However, in another embodiment the film is oriented to the same extent in both the MD and TD directions.

The films may vary in thickness depending on the intended application; however, films of a thickness from 1 to 50 µm are usually suitable. Films intended for packaging are usually from 10 to 50 µm thick. The thickness of the sealing layer is typically 0.2 to 50 µm. There may be a sealing layer on both the inner and outer surfaces of the film or the sealing layer may be present on only the inner or the outer surface.

In another embodiment, one or more layers may be modified by corona treatment, electron beam irradiation, gamma irradiation, flame treatment, or microwave. In a preferred embodiment, one or both of the surface layers is modified by corona treatment.

EXPERIMENTAL

MAO is methyl alumoxane (30 wt % in toluene) obtained from Albemarle.

TNOAL is tri-n-octyl aluminum.

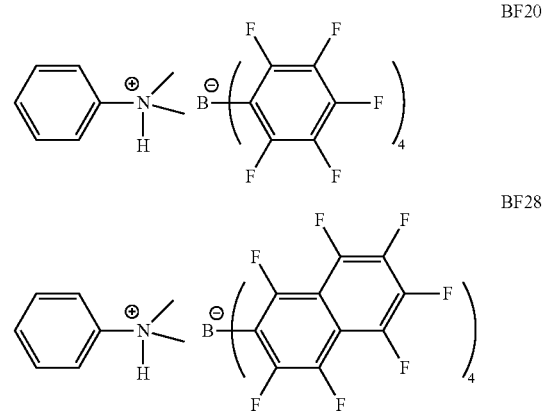

MCN-1 is dimethylsilyl (4-o-biphenyl-2-butyl indenyl) (4-(3',5'-di-tert-butyl-4'-methoxyphenyl)-2-methyl-1,5,6,7-tetrahydro-s-indacenyl) Zr dimethyl.

MCN2 is dimethylsilyl bis-indenyl hafnium dimethyl.

MCN3 is dimethylsilyl (4-phenyl-2-methyl-indacenyl) (2-isopropyl-4-(4-tert-butyl-phenyl)-indenyl) zirconium dimethyl.

MCN4 is dimethylsilyl (4(4'-tert-butyl-phenyl)-2-methyl-indenyl) (2-isopropyl-4-(4'-tert-butyl-phenyl)-indenyl) zirconium dimethyl.

MCN5 is dimethylsilyl bis(4-phenyl-2-methyl-indenyl) zirconium dimethyl.

MCN6 is dimethylsilyl bis(4-phenyl-2-methyl-indenyl) hafnium dimethyl.

MCN7 is dimethylsilyl bis(4-N-carbazolyl-2-methyl-indenyl) zirconium dimethyl.

MCN8 is dimethylsilyl (4-o-biphenyl-2-hexyl indenyl) (4-(3,5-di-tert-butyl-4-methoxyphenyl)-2-methyl indenyl) Hf dimethyl.

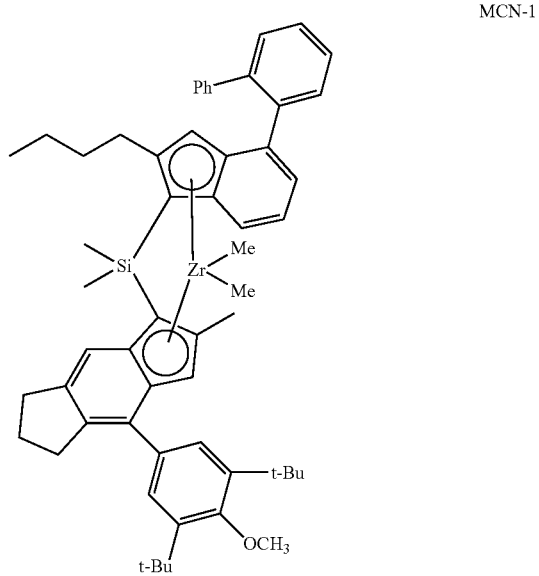

-continued

MCN-8

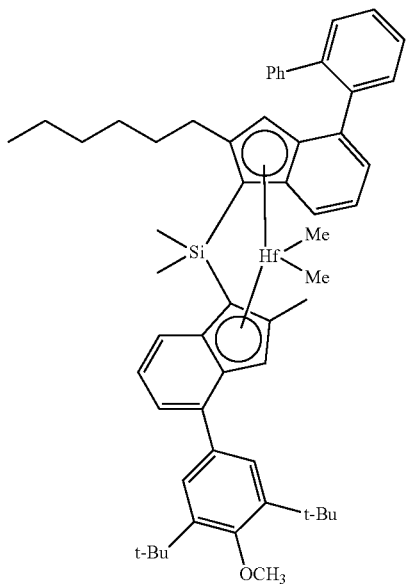

Metallocene Synthesis:

MCN1

Dimethylsilyl(4-o-biphenyl-2-butyl indenyl)(4-(3',5'-di-tert-butyl-4'-methoxyphenyl)-2-methyl-1,5,6,7-tetrahydro-s-indacenyl)zirconium dimethyl: A precooled solution of rac-dimethylsilyl (4-o-biphenyl-2-butyl indenyl) (4-(3,5-di-tert-butyl-4-methoxyphenyl)-2-methyl-1,5,6,7-tetrahydro-s-indacenyl) zirconium dichloride (synthesized as described in PCT/US2016/034784) (600 mg, 0.648 mmol) in 20 mL of diethyl ether was treated with methyl lithium (1.6 M in hexane, 0.83 mL, 1.33 mmol), and the reaction was stirred for 19 hours at room temperature. Then the solvents were evaporated and the residue was extracted with hexane (2×50 mL). The collected filtrate was concentrated to the volume was 10 mL and then filtered to obtain a green-yellow solid as the (378 mg, ratio of rac/meso>50:1). 1H NMR (400 MHz, $C_6D_6$, 23° C.): δ 7.89-7.83 (m, 1 H), 7.75 (s, 2 H), 7.43-7.39 (m, 2 H), 7.32 (d, 1 H), 7.25-7.21 (m, 2 H), 7.18-7.08 (m, 3 H), 7.02 (s, 1 H), 6.98-6.91 (m, 2 H), 6.90-6.86 (m, 1 H), 6.93 (s, 1 H), 6.91 (dd, 1 H), 3.45 (s, 3 H), 3.10-2.63 (m, 5 H), 2.20-2.10 (m, 1 H), 1.91 (s, 3 H), 1.90-1.69 (m, 2 H), 1.52 (s, 18 H), 1.40-1.16 (m, 4 H), 0.95-0.85 (m, 6 H), 0.68 (s, 3 H), −0.62 (s, 3 H), −0.67 (s, 3 H).

MCN8

Dimethylsilyl(4-o-biphenyl-2-hexyl indenyl)(4-(3,5-di-tert-butyl-4-methoxyphenyl)-2-methyl indenyl) Hf dimethyl: A precooled solution of dilithium dimethylsilyl (4-o-biphenyl-2-nHexyl indenide) (4-(3',5'-di-tert-butyl-4'-methoxy-phenyl)-2-methyl indenide (3.1 g, 4.03 mmol) in diethyl ether (20 mL) was treated with HfCl4 (1.291 g, 4.03 mmol). The mixture was stirred at room temperature for 18 h. The mixture was evaporated to dryness and was extracted with toluene (30 mL). Toluene extract was evaporated to dryness. The residue was washed with hexane to get a solid as a mixture of two isomers (rac/meso=1.6/1). The mixture was recrystallized from toluene (20 mL, 80° C. to r.t.) to get a solid and the solid was washed with 2 mL of hexane to give a mixture of meso/rac (1.75:1, 1.02 g). The filtrate was concentrated and recrystallized (15 mL of toluene and 10 mL of hexane, refluxed to room temperature) to afford the dimethylsilyl (4-o-biphenyl-2-hexyl indenyl) (4-(3',5'-di-tert-butyl-4'-methoxyphenyl)-2-methyl indenyl) Hf dichloride with rac/meso of 18:1 (1.136 g). A precooled solution of the above dichloride compound (524 mg, 0.52 mmol, rac/meso=18:1) in 20 mL of diethyl ether was treated with methyl lithium (1.6 M in hexane, 0.65 mL, 1.04 mmol), and the reaction was stirred for 20 hours at room temperature. Then the solvents were evaporated and the residue was extracted with mixed solvents (16 mL of hexane and 4 mL of toluene, twice). The collected filtrate was concentrated and the solid was crystallized (3 mL of hexane and 20 mL of toluene, refluxed to −35° C.) to obtain a white solid as the product (290 mg, ratio of rac/meso=22:1). 1H NMR (400 MHz, $C_6D_6$, 23° C.): δ 7.98-7.84 (m, 3 H), 7.56 (d, 1 H), 7.42-7.34 (m, 3 H), 7.23-7.18 (m, 2 H), 7.16-7.11 (m, 3 H), 7.02-6.87 (m, 5 H), 6.72 (dd, 1 H), 6.69 (s, 1 H), 3.39 (s, 3 H), 2.73-2.63 (m, 1 H), 2.20-2.10 (m, 1 H), 1.95 (s, 3 H), 1.51 (s, 18 H), 1.40-1.16 (m, 8 H), 0.93 (t, 3 H), 0.86 (s, 3 H), 0.66 (s, 3 H), −0.74 (s, 3 H), −0.81 (s, 3 H).

General Procedure for Small Scale Polymerization

Unless stated otherwise propylene homopolymerization and ethylene-propylene copolymerizations are carried out in a parallel pressure reactor, as generally described in U.S. Pat. Nos. 6,306,658; 6,455,316; WO 00/09255; and Murphy et al., J. Am. Chem. Soc., 2003, 125, pp. 4306-4317, each of which is incorporated by reference herein in its entirety. Although specific quantities, temperatures, solvents, reactants, reactants ratios, pressures, and other variables may need to be adjusted from one reaction to the next, the following describes a typical polymerization performed in a parallel, pressure reactor.

For propylene polymerization and ethylene propylene copolymerization with unsupported metallocene catalysts, the following procedure was used.

A pre-weighed glass vial insert and disposable stirring paddle were fitted to each reaction vessel of the reactor, which contains 48 individual reaction vessels. The reactor was then closed and propylene gas was introduced to each vessel to purge the nitrogen out of the system. If any modules receive hydrogen, it was added in during the purge process. The solvent (typically isohexane) was added next according to the set total reaction volume, including the following additions, to 5 mL usually. At this time scavenger and/or co-catalyst and/or a chain transfer agent, such as tri-n-octylaluminum in toluene (100-1000 nmol) was added. The contents of the vessels were stirred at 800 rpm. The propylene was added as gas to a set pressure. The reactor vessels were heated to their set run temperature (usually between 50° C. and 110° C.). If any modules receive ethylene, it was added as a gas to a pre-determined pressure (typically 5-220 psi) above the pressure of the propylene while the reactor vessels were heated to a set run temperature.

A toluene solution of catalyst (typically at a concentration of 0.2 mmol/L in toluene which usually provides about 15 nmol of catalyst) was injected into the reactors. The reaction was then allowed to proceed until a pre-determined amount of pressure had been taken up by the reaction. Alternatively, the reaction may be allowed to proceed for a set amount of time. The reaction was quenched by pressurizing the vessel with compressed air. After the polymerization reaction, the glass vial insert containing the polymer product and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight and by DSC (see below) to determine melting point.

To determine various molecular weight related values by GPC, high temperature size exclusion chromatography was performed using an automated "Rapid GPC" system as generally described in U.S. Pat. Nos. 6,491,816; 6,491,823; 6,475,391; 6,461,515; 6,436,292; 6,406,632; 6,175,409; 6,454,947; 6,260,407; and 6,294,388; each of which is fully incorporated herein by reference for US purposes. This apparatus has a series of three 30 cm×7.5 mm linear columns, each containing PLgel 10 um, Mix B. The GPC system was calibrated using polystyrene standards ranging from 580-3,390,000 g/mol. The system was operated at an eluent flow rate of 2.0 mL/minutes and an oven temperature of 165° C. 1,2,4-trichlorobenzene was used as the eluent. The polymer samples were dissolved in 1,2,4-trichlorobenzene at a concentration of 0.1-0.9 mg/mL. 250 uL of a polymer solution was injected into the system. The concentration of the polymer in the eluent was monitored using a Polymer Char IR4 detector. The molecular weights presented are relative to linear polystyrene standards and are uncorrected. For purposes of this invention only, the Rapid-GPC Mw (weight average molecular weight) data can be divided by 1.9 to approximate GPC-3D Mw results for ethylene-propylene copolymers. Likewise, for purposes of this invention only, the Rapid-GPC Mw data for propylene homopolymers can be divided by 1.5 to approximate GPC-3D Mw results.

Differential Scanning Calorimetry (DSC Procedure-1) measurements were performed on a TA-Q200 instrument to determine the melting point of the polymers. Samples were pre-annealed at 220° C. for 15 minutes and then allowed to cool to room temperature overnight. The samples were then heated to 220° C. at a rate of 100° C./minutes and then cooled at a rate of 50° C./min. Melting points were collected during the heating period.

The amount of ethylene incorporated in the polymers (weight %) was determined by rapid FT-IR spectroscopy on a Bruker Vertex 70 IR in reflection mode. Samples were prepared in a thin film format by evaporative deposition techniques. Weight percent ethylene was obtained from the ratio of peak heights at 729.8 and 1157.9 cm-1. This method was calibrated using a set of ethylene/propylene copolymers with a range of known wt % ethylene content.

Differential Scanning Calorimetry (for larger scale products) (DSC-Procedure-2). Peak melting point, (Tm, also referred to as melting point), peak crystallization temperature (Tc, also referred to as crystallization temperature), glass transition temperature (Tg), heat of fusion (Hf), and percent crystallinity were determined using the following DSC procedure according to ASTM D3418-03. Differential scanning calorimetric (DSC) data were obtained using a TA Instruments model Q2100 machine. Samples weighing approximately 5-10 mg were sealed in an aluminum hermetic sample pan. The DSC data were recorded by first gradually heating the sample to 200° C. at a rate of 10° C./minute. The sample was kept at 200° C. for 2 minutes, then cooled to −70° C. at a rate of 10° C./minute, followed by an isothermal for 2 minutes and heating to 200° C. at 10° C./minute. Both the first and second cycle thermal events were recorded. Areas under the endothermic peaks were measured and used to determine the heat of fusion and the percent of crystallinity. The percent crystallinity is calculated using the formula, [area under the melting peak (Joules/gram)/B (Joules/gram)]*100, where B is the heat of fusion for the 100% crystalline homopolymer of the major monomer component. These values for B are to be obtained from the Polymer Handbook, Fourth Edition, published by John Wiley and Sons, New York 1999, provided, however, that a value of 189 J/g is used as the heat of fusion for 100% crystalline polypropylene, a value of 290 J/g is used for the heat of fusion for 100% crystalline polyethylene. The melting and crystallization temperatures reported here were obtained during the first cooling/second heating cycle unless otherwise noted.

In the event of conflict between the DSC Procedure-1 and DSC procedure-2, DSC procedure-2 shall be used.

Gel Permeation Chromatography with Three Detectors (GPC-3D)

Mw, Mn and Mw/Mn are determined by using a High Temperature Gel Permeation Chromatography (Agilent PL-220), equipped with three in-line detectors, a differential refractive index detector (DRI), a light scattering (LS) detector, and a viscometer. Experimental details, including detector calibration, are described in: T. Sun, P. Brant, R. R. Chance, and W. W. Graessley, Macromolecules, Volume 34, Number 19, pp. 6812-6820, (2001) and references therein. Three Agilent PLgel 10 m Mixed-B LS columns are used. The nominal flow rate is 0.5 mL/min, and the nominal injection volume is 300 μL. The various transfer lines, columns, viscometer and differential refractometer (the DRI detector) are contained in an oven maintained at 145° C. Solvent for the experiment is prepared by dissolving 6 grams of butylated hydroxytoluene as an antioxidant in 4 liters of Aldrich reagent grade 1,2,4-trichlorobenzene (TCB). The TCB mixture is then filtered through a 0.1 μm Teflon filter. The TCB is then degassed with an online degasser before entering the GPC-3D. Polymer solutions are prepared by placing dry polymer in a glass container, adding the desired amount of TCB, then heating the mixture at 160° C. with continuous shaking for about 2 hours. All quantities are measured gravimetrically. The TCB densities used to express the polymer concentration in mass/volume units are 1.463 g/ml at room temperature and 1.284 g/ml at 145° C. The injection concentration is from 0.5 to 2.0 mg/ml, with lower concentrations being used for higher molecular weight samples. Prior to running each sample the DRI detector and the viscometer are purged. Flow rate in the apparatus is then increased to 0.5 ml/minute, and the DRI is allowed to stabilize for 8 hours before injecting the first sample. The LS laser is turned on at least 1 to 1.5 hours before running the samples. The concentration, c, at each point in the chromatogram is calculated from the baseline-subtracted DRI signal, $I_{DRI}$, using the following equation:

$$c = K_{DRI} I_{DRI}/(dn/dc)$$

where $K_{DRI}$ is a constant determined by calibrating the DRI, and (dn/dc) is the refractive index increment for the system. The refractive index, n=1.500 for TCB at 145° C. and λ=690 nm. Units on parameters throughout this description of the GPC-3D method are such that concentration is expressed in g/cm$^3$, molecular weight is expressed in g/mole, and intrinsic viscosity is expressed in dL/g.

The LS detector is a Wyatt Technology High Temperature DAWN HELEOS. The molecular weight, M, at each point in the chromatogram is determined by analyzing the LS output using the Zimm model for static light scattering (M. B. Huglin, LIGHT SCATTERING FROM POLYMER SOLUTIONS, Academic Press, 1971):

$$\frac{K_o c}{\Delta R(\theta)} = \frac{1}{MP(\theta)} + 2A_2 c.$$

Here, $\Delta R(\theta)$ is the measured excess Rayleigh scattering intensity at scattering angle $\theta$, c is the polymer concentration determined from the DRI analysis, $A_2$ is the second virial coefficient. $P(\theta)$ is the form factor for a monodisperse random coil, and $K_o$ is the optical constant for the system:

$$K_o = \frac{4\pi^2 n^2 (dn/dc)^2}{\lambda^4 N_A}$$

where $N_A$ is Avogadro's number, and (dn/dc) is the refractive index increment for the system, which take the same value as the one obtained from DRI method. The refractive index, n=1.500 for TCB at 145° C. and λ=657 nm.

A high temperature Viscotek Corporation viscometer, which has four capillaries arranged in a Wheatstone bridge configuration with two pressure transducers, is used to determine specific viscosity. One transducer measures the total pressure drop across the detector, and the other, positioned between the two sides of the bridge, measures a differential pressure. The specific viscosity, $\eta_s$, for the solution flowing through the viscometer is calculated from their outputs. The intrinsic viscosity, [η], at each point in the chromatogram is calculated from the following equation:

$$\eta_s = c[\eta] + 0.3(c[\eta])^2$$

where c is concentration and was determined from the DRI output.

The branching index ($g'_{vis}$) is calculated using the output of the GPC-DRI-LS-VIS method as follows. The average intrinsic viscosity, $[\eta]_{avg}$, of the sample is calculated by:

$$[\eta]_{avg} = \frac{\sum c_i [\eta]_i}{\sum c_i}$$

where the summations are over the chromatographic slices, i, between the integration limits. The branching index $g'_{vis}$ is defined as:

$$g'vis = \frac{[\eta]_{avg}}{kM_v^\alpha}.$$

$M_v$ is the viscosity-average molecular weight based on molecular weights determined by LS analysis. Z average branching index ($g'_{Zave}$) is calculated using Ci=polymer concentration in the slice i in the polymer peak times the mass of the slice squared, $Mi^2$.

The Mark-Houwink parameters used in the data processing for the tested samples are: 1) for ethylene polymers: K/a=0.000579/0.695; and 2) for propylene polymers: K/a=0.0002288/0.705).

All molecular weights are weight average unless otherwise noted. All molecular weights are reported in g/mol unless otherwise noted.

In the event of conflict between the GPC-3D procedure and the "Rapid GPC," the GPC-3D procedure immediately above shall be used. Further details regarding methods of determining Mw, Mn, MWD are described in US 2006/0173123 pages 24-25, paragraphs [0334] to [0341].

1% Secant flexural modulus is measured using an ISO 37-Type 3 bar, with a crosshead speed of 1.0 mm/min and a support span of 30.0 mm using an Instron machine according to ASTM D 790 (A, 1.0 mm/min).

Ethylene-Propylene Copolymerizations

Figure 2:
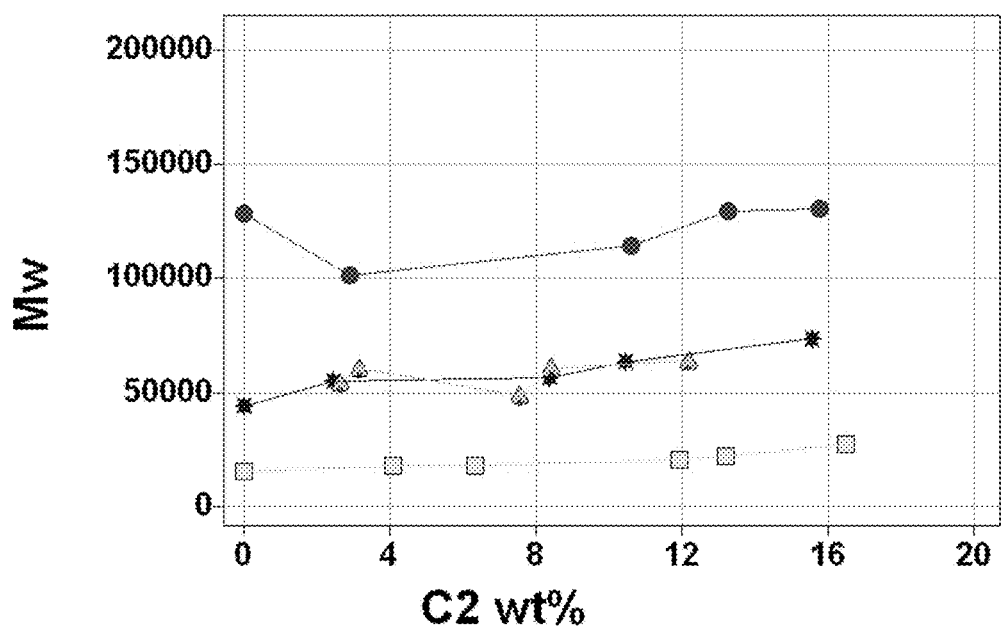
FIG. 2 shows a plot of weight average molecular weight (g/mol) versus ethylene content (wt %) for ethylene-propylene copolymer produced at 100° C. using catalysts prepared using BF20 activator. Symbols Used: MCN-1 (circle), MCN-2 (star), MCN-4 (square), MCN-8 (spade). Lines connecting data points are to aid visualization and have no other significance.

A series of ethylene propylene copolymerizations targeting compositions containing 0-20 wt % ethylene were performed in parallel pressure reactors (PPRs) developed by Symyx Technologies, Inc. In these studies eight different metallocenes, MCN-1 through MCN-8, and two different borate activators, N,N-dimethylanilinium tetrakis(perfluorophenyl)borate (BF20) and N,N-dimethylanilinium tetrakis (perfluoronaphthalene-2-yl)borate (BF28), were used. Polymerizations were performed at 85° C. and 100° C. The data collected for each metallocene/activator combination at a certain process temperature are evaluated by comparing the weight-average molecular weight ($M_w$) of the polymer produced versus the weight percent ethylene ($C_2$ wt %) of the polymer. When comparisons are made, the preferred catalyst system is that which produces the higher Mw product in the composition range of interest, which is generally 4-20 wt % ethylene.FIG 1 shows a plot of weight average molecular weight (g/mol) versus ethylene content (wt %)for ethylene-propylene copolymer produced at 85°C. FIG. 2 shows a plot of weight average molecular weight (g/mol) versus ethylene content (wt %) for ethylene-propylene copolymer produced at 100°C.

Polymerization at 85° C.

Figure 3:
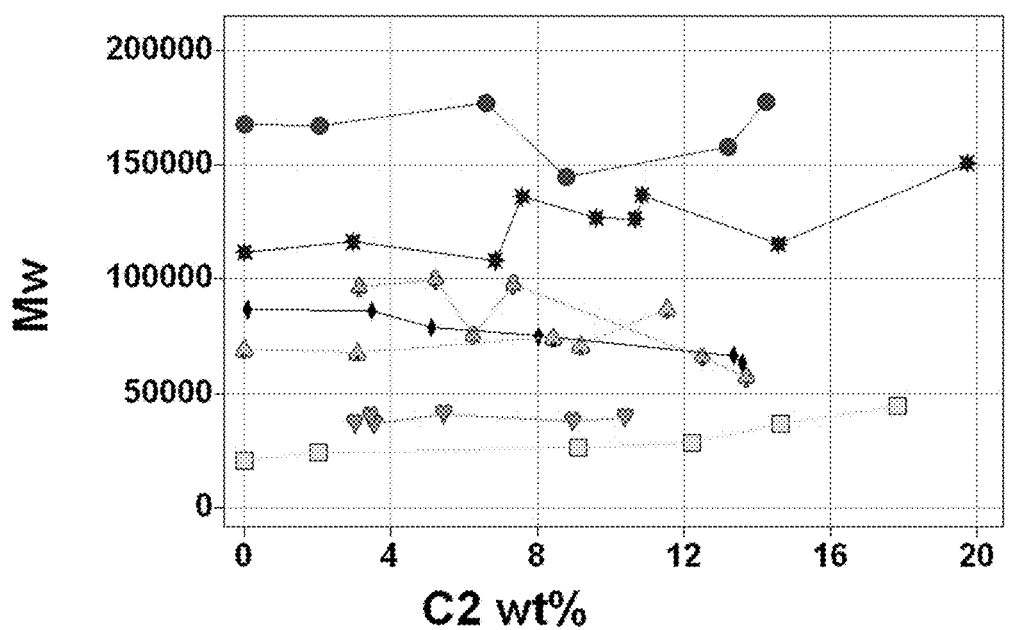
FIG. 3 shows a plot of weight average molecular weight (g/mol) versus ethylene content (wt %) for ethylene-propylene copolymer produced at 100° C. using catalysts prepared using BF28 activator. Symbols Used: MCN-1 (circle), MCN-2 (star), MCN-4 (square), MCN-5 (diamond), MCN-6 (heart), MCN-7 (club), MCN-8 (spade). Lines connecting data points are to aid visualization and have no other significance.
Figure 4:
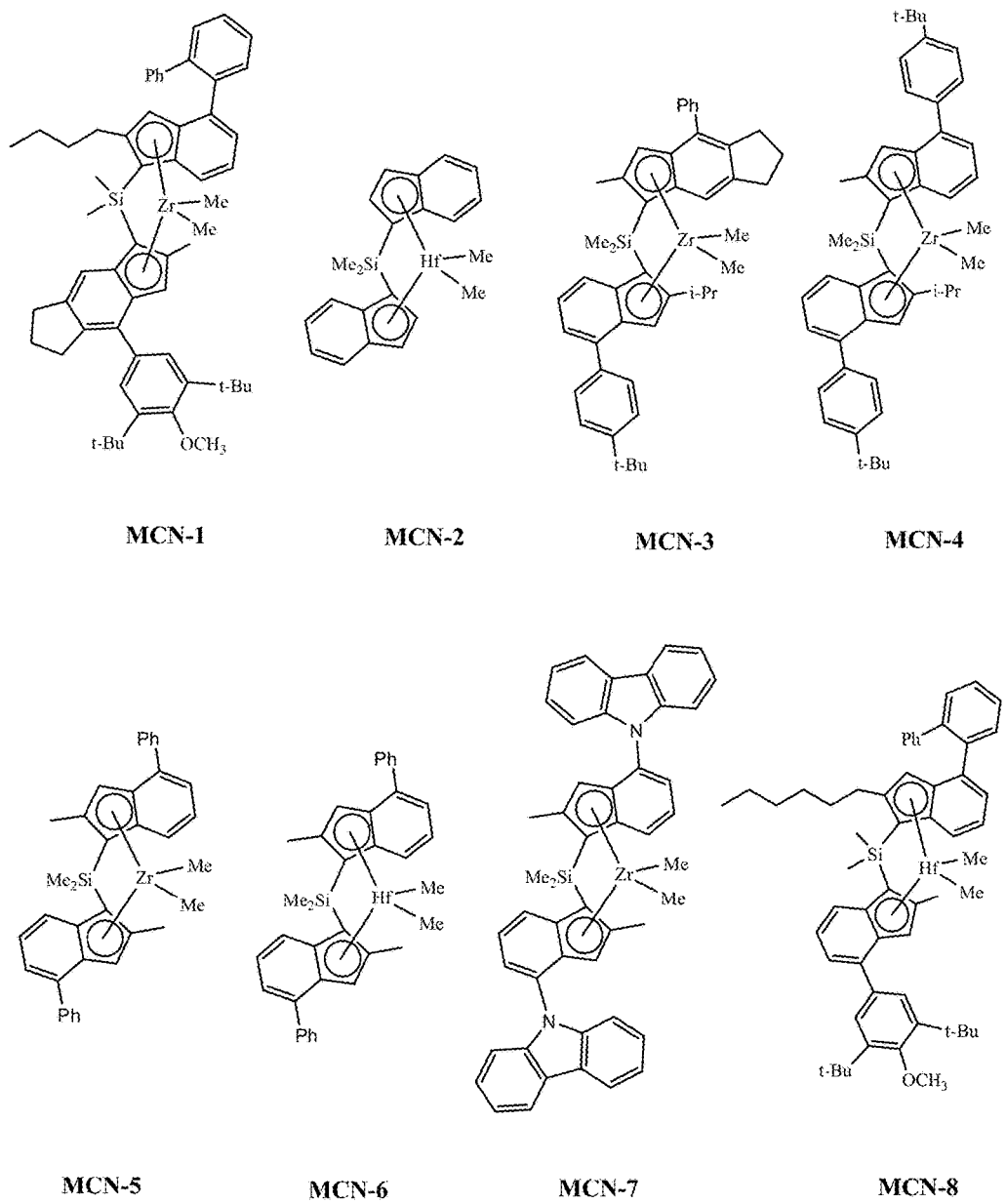
FIG. 4 shows drawings of catalyst compounds useful herein.

Ethylene and propylene were copolymerized at 85° C. using catalysts formed by reaction of BF28 activator with each of MCN-1, MCN-2, and MCN-3. Additionally, runs were performed using MCN-3 activated with BF20. The data for these runs are presented in Table 1. Data presented as a plot of Mw versus $C_2$ wt % for each of the runs reveal that MCN-1 and MCN-2 have higher molecular weight capability than MCN-3 (FIG. 3) for compositions containing 20 wt % or less ethylene.

Polymerization at 100° C.

Ethylene and propylene were copolymerized at 100° C. using catalysts formed by reaction of BF20 activator with each of MCN-1, MCN-2, MCN-4, and MCN-8. Additionally, runs were performed using each of MCN-1, MCN-2, MCN-4, MCN-5, MCN-6, MCN-7, and MCN-8 activated with BF28. The data for these runs are presented in Table 1. Data presented as a plot of Mw versus $C_2$ wt % for the polymer produced in the runs using BF20 activator (FIG. 2) indicate that MCN-1 has higher molecular weight capability than MCN-2, MCN-4, or MCN-8. Data presented as a plot of Mw versus $C_2$ wt % for the polymer produced in the runs using BF28 activator (FIG. 3) indicate MCN-1 has higher molecular weight capability than MCN-2, MCN-4, MCN-5, MCN-6, MCN-7, or MCN-8. Comparing the data for MCN-1 activated with BF20 to that for BF28 shows that the MCN-1/BF28 combination has greater molecular weight capability than MCN-1/BF20.

TABLE 1

Data for the copolymerization of ethylene and propylene performed at 85° C.

| Run | MCN-# | act | C2 (psi) | quench t (s) | yield (mg) | A (kg/mmol/h) | ethylene wt % | Mw | Mn | PDI | Tm |
|---|---|---|---|---|---|---|---|---|---|---|---|
| 1 | MCN-1 | BF28 | 0 | 50 | 148 | 707 | 0.0 | 331,052 | 153,661 | 2.2 | 157 |
| 2 | MCN-1 | BF28 | 0 | 32 | 111 | 841 | 0.0 | 308,418 | 157,874 | 2.0 | 157 |
| 3 | MCN-1 | BF28 | 5 | 36 | 192 | 1,279 | 1.0 | 284,659 | 103,070 | 2.8 | 142 |
| 4 | MCN-1 | BF28 | 5 | 31 | 185 | 1,452 | 0.0 | 261,737 | 119,395 | 2.2 | 142 |
| 5 | MCN-1 | BF28 | 10 | 28 | 190 | 1,650 | 3.5 | 316,822 | 113,283 | 2.8 | 124 |
| 6 | MCN-1 | BF28 | 10 | 26 | 185 | 1,703 | 3.9 | 290,744 | 119,269 | 2.4 | 122 |
| 7 | MCN-1 | BF28 | 20 | 17 | 240 | 3,352 | 8.9 | 242,446 | 67,984 | 3.6 | 105 |
| 8 | MCN-1 | BF28 | 20 | 19 | 232 | 2,940 | 9.7 | 238,060 | 75,972 | 3.1 | 105 |
| 9 | MCN-1 | BF28 | 40 | 16 | 257 | 3,790 | 9.9 | 263,302 | 71,518 | 3.7 | |
| 10 | MCN-1 | BF28 | 80 | 6 | 233 | 9,328 | 16.3 | 318,919 | 74,426 | 4.3 | |
| 11 | MCN-1 | BF28 | 80 | 7 | 261 | 9,346 | 14.4 | 319,548 | 65,433 | 4.9 | |
| 12 | MCN-2 | BF28 | 0 | 127 | 35 | 66 | 0.0 | 275,391 | 156,460 | 1.8 | 133 |
| 13 | MCN-2 | BF28 | 0 | 503 | 26 | 12 | 0.0 | 315,341 | 163,965 | 1.9 | 134 |
| 14 | MCN-2 | BF28 | 5 | 63 | 49 | 188 | 4.8 | 260,808 | 147,897 | 1.8 | 101 |
| 15 | MCN-2 | BF28 | 5 | 129 | 42 | 78 | 4.7 | 305,295 | 167,210 | 1.8 | 99 |
| 16 | MCN-2 | BF28 | 10 | 56 | 50 | 213 | 7.2 | 274,978 | 147,278 | 1.9 | 77 |
| 17 | MCN-2 | BF28 | 10 | 82 | 53 | 155 | 6.2 | 271,536 | 145,958 | 1.9 | 75 |
| 18 | MCN-2 | BF28 | 20 | 35 | 75 | 514 | 16.2 | 253,163 | 146,860 | 1.7 | |
| 19 | MCN-2 | BF28 | 20 | 41 | 70 | 410 | 13.1 | 270,896 | 160,733 | 1.7 | |
| 20 | MCN-3 | BF20 | 0 | 319 | 27 | 20 | 0.0 | 63,037 | 37,209 | 1.7 | 155 |
| 21 | MCN-3 | BF20 | 0 | 325 | 30 | 22 | 0.0 | 57,142 | 33,777 | 1.7 | 153 |
| 22 | MCN-3 | BF20 | 5 | 174 | 34 | 46 | 0.6 | 74,772 | 43,195 | 1.7 | 138 |
| 23 | MCN-3 | BF20 | 5 | 132 | 54 | 99 | 2.6 | 72,574 | 42,608 | 1.7 | 138 |
| 24 | MCN-3 | BF20 | 10 | 110 | 54 | 118 | 4.0 | 76,739 | 41,918 | 1.8 | 119 |
| 25 | MCN-3 | BF20 | 10 | 101 | 70 | 166 | 2.5 | 72,398 | 41,314 | 1.8 | 120 |
| 26 | MCN-3 | BF20 | 20 | 65 | 81 | 300 | 9.1 | 75,109 | 43,213 | 1.7 | 95 |
| 27 | MCN-3 | BF20 | 20 | 71 | 92 | 309 | 10.2 | 77,257 | 45,360 | 1.7 | 96 |
| 28 | MCN-3 | BF20 | 40 | 34 | 128 | 898 | 16.4 | 93,626 | 50,523 | 1.9 | |
| 29 | MCN-3 | BF20 | 40 | 71 | 68 | 230 | 11.8 | 108,275 | 61,179 | 1.8 | |
| 30 | MCN-3 | BF20 | 40 | 78 | 82 | 253 | 8.6 | 106,759 | 65,772 | 1.6 | |
| 31 | MCN-3 | BF20 | 80 | 23 | 145 | 1,490 | 19.5 | 110,503 | 46,826 | 2.4 | |
| 32 | MCN-3 | BF20 | 80 | 26 | 134 | 1,257 | 16.3 | 114,267 | 65,638 | 1.7 | |
| 33 | MCN-3 | BF20 | 80 | 28 | 152 | 1,326 | 19.4 | 112,922 | 54,104 | 2.1 | |
| 34 | MCN-3 | BF28 | 0 | 340 | 29 | 20 | 0.0 | 80,903 | 47,158 | 1.7 | 154 |
| 35 | MCN-3 | BF28 | 0 | 334 | 25 | 18 | 0.0 | 85,503 | 50,865 | 1.7 | 154 |
| 36 | MCN-3 | BF28 | 5 | 219 | 41 | 45 | 3.8 | 103,624 | 61,284 | 1.7 | 138 |
| 37 | MCN-3 | BF28 | 5 | 198 | 37 | 45 | 3.0 | 100,689 | 56,962 | 1.8 | 136 |
| 38 | MCN-3 | BF28 | 10 | 159 | 36 | 55 | 6.4 | 109,517 | 66,484 | 1.6 | 116 |
| 39 | MCN-3 | BF28 | 10 | 325 | 22 | 16 | 4.2 | 111,103 | 61,753 | 1.8 | 119 |
| 40 | MCN-3 | BF28 | 20 | 161 | 38 | 57 | 8.6 | 136,237 | 79,651 | 1.7 | 86 |
| 41 | MCN-3 | BF28 | 20 | 86 | 77 | 216 | 6.9 | 113,143 | 57,817 | 2.0 | 93 |
| 42 | MCN-3 | BF28 | 40 | 71 | 77 | 259 | 12.9 | 153,771 | 83,017 | 1.9 | |
| 43 | MCN-3 | BF28 | 40 | 80 | 85 | 257 | 10.8 | 159,946 | 94,234 | 1.7 | |
| 44 | MCN-3 | BF28 | 40 | 69 | 76 | 264 | 9.2 | 132,053 | 79,577 | 1.7 | |
| 45 | MCN-3 | BF28 | 80 | 34 | 122 | 870 | 19.6 | 186,770 | 100,394 | 1.9 | |

General conditions: propylene = 140 psi; metallocene = 15 nmol; activator = 16.5 nmol; solvent = hexanes; total volume = 5 mL; tri(n-octyl)aluminum = 500 nmol.
Abbreviations: MCN is metallocene, act is activator, $C_2$ is ethylene, t is time, A is catalyst activity, Mw is weight average molecular weight, Mn is number average molecular weight, PDI is polydispersity defined as Mw/Mn, and Tm is melting point.

TABLE 2

Data for the copolymerization of ethylene and propylene performed at 100° C.

| Run | MCN-# | act | C2 (psi) | quench time (s) | yield (mg) | A (kg/mmol/h) | ethylene wt % | Mw | Mn | PDI | Tm |
|---|---|---|---|---|---|---|---|---|---|---|---|
| 1 | MCN-1 | BF20 | 0 | 33 | 152 | 1,099 | 0.0 | 128,000 | 62,111 | 2.1 | 156 |
| 2 | MCN-1 | BF20 | 5 | 17 | 194 | 2,758 | 2.9 | 101,362 | 29,401 | 3.4 | 138 |
| 3 | MCN-1 | BF20 | 20 | 10 | 205 | 5,120 | 10.6 | 114,160 | 32,085 | 3.6 | 102 |
| 4 | MCN-1 | BF20 | 30 | 7 | 219 | 7,399 | 13.3 | 129,488 | 30,167 | 4.3 | |
| 5 | MCN-1 | BF20 | 40 | 6 | 165 | 7,209 | 15.8 | 130,284 | 25,935 | 5.0 | |
| 6 | MCN-1 | BF28 | 0 | 22 | 96 | 1,029 | 0.0 | 167,815 | 77,948 | 2.2 | 156 |
| 7 | MCN-1 | BF28 | 5 | 25 | 154 | 1,497 | 2.1 | 166,997 | 74,077 | 2.3 | 144 |
| 8 | MCN-1 | BF28 | 10 | 15 | 159 | 2,486 | 6.6 | 177,176 | 52,216 | 3.4 | 118 |
| 9 | MCN-1 | BF28 | 20 | 11 | 176 | 3,873 | 8.8 | 144,813 | 47,250 | 3.1 | 100 |
| 10 | MCN-1 | BF28 | 30 | 13 | 216 | 4,076 | 13.2 | 157,972 | 40,612 | 3.9 | |
| 11 | MCN-1 | BF28 | 40 | 10 | 210 | 4,844 | 14.3 | 177,381 | 46,164 | 3.8 | |
| 12 | MCN-2 | BF20 | 0 | 96 | 41 | 103 | 0.0 | 44,343 | 22,492 | 2.0 | 114 |
| 13 | MCN-2 | BF20 | 5 | 58 | 50 | 210 | 2.4 | 55,088 | 31,310 | 1.8 | 118 |
| 14 | MCN-2 | BF20 | 10 | 40 | 65 | 391 | 8.4 | 56,681 | 32,213 | 1.8 | 85 |
| 15 | MCN-2 | BF20 | 20 | 31 | 82 | 638 | 10.5 | 63,555 | 34,329 | 1.9 | |

TABLE 2-continued

Data for the copolymerization of ethylene and propylene performed at 100° C.

| Run | MCN-# | act | C2 (psi) | quench time (s) | yield (mg) | A (kg/mmol/h) | ethylene wt % | Mw | Mn | PDI | Tm |
|---|---|---|---|---|---|---|---|---|---|---|---|
| 16 | MCN-2 | BF20 | 30 | 21 | 88 | 1,017 | 15.6 | 73,487 | 36,085 | 2.0 | |
| 17 | MCN-2 | BF28 | 0 | 97 | 63 | 155 | 0.0 | 111,668 | 62,608 | 1.8 | 122 |
| 18 | MCN-2 | BF28 | 5 | 61 | 75 | 292 | 3.0 | 116,117 | 72,390 | 1.6 | 105 |
| 19 | MCN-2 | BF28 | 10 | 79 | 67 | 203 | 6.9 | 107,966 | 62,600 | 1.7 | 82 |
| 20 | MCN-2 | BF28 | 10 | 84 | 46 | 131 | 9.6 | 126,663 | 79,111 | 1.6 | 84 |
| 21 | MCN-2 | BF28 | 10 | 55 | 63 | 275 | 10.9 | 136,739 | 77,085 | 1.8 | |
| 22 | MCN-2 | BF28 | 20 | 47 | 74 | 378 | 10.7 | 126,105 | 75,023 | 1.7 | 53 |
| 23 | MCN-2 | BF28 | 20 | 50 | 70 | 336 | 7.6 | 135,911 | 78,911 | 1.7 | 80 |
| 24 | MCN-2 | BF28 | 20 | 26 | 105 | 964 | 14.6 | 115,111 | 58,309 | 2.0 | |
| 25 | MCN-2 | BF28 | 40 | 18 | 104 | 1,389 | 19.7 | 150,800 | 84,243 | 1.8 | |
| 26 | MCN-4 | BF20 | 0 | 237 | 43 | 43 | 0.0 | 15,767 | 8,954 | 1.8 | 140 |
| 27 | MCN-4 | BF20 | 5 | 95 | 50 | 125 | 4.1 | 18,403 | 10,016 | 1.8 | 122 |
| 28 | MCN-4 | BF20 | 10 | 91 | 76 | 201 | 6.4 | 18,326 | 10,726 | 1.7 | 111 |
| 29 | MCN-4 | BF20 | 20 | 61 | 77 | 304 | 11.9 | 20,997 | 11,971 | 1.8 | |
| 30 | MCN-4 | BF20 | 30 | 41 | 95 | 559 | 13.2 | 22,132 | 11,130 | 2.0 | |
| 31 | MCN-4 | BF20 | 40 | 42 | 89 | 504 | 16.5 | 27,463 | 14,750 | 1.9 | |
| 32 | MCN-4 | BF28 | 0 | 183 | 34 | 45 | 0.0 | 20,917 | 11,491 | 1.8 | 141 |
| 33 | MCN-4 | BF28 | 5 | 164 | 53 | 78 | 2.0 | 24,243 | 11,523 | 2.1 | 134 |
| 34 | MCN-4 | BF28 | 10 | 102 | 63 | 147 | 9.1 | 26,525 | 12,536 | 2.1 | 106 |
| 35 | MCN-4 | BF28 | 20 | 63 | 82 | 314 | 12.2 | 28,530 | 14,752 | 1.9 | |
| 36 | MCN-4 | BF28 | 30 | 48 | 95 | 475 | 14.6 | 36,652 | 17,043 | 2.2 | |
| 37 | MCN-4 | BF28 | 40 | 39 | 89 | 545 | 17.8 | 44,513 | 25,180 | 1.8 | |
| 38 | MCN-5 | BF28 | 10 | 25 | 99 | 957 | 0.1 | 86,721 | 42,399 | 2.0 | 142 |
| 39 | MCN-5 | BF28 | 10 | 37 | 148 | 972 | 3.5 | 85,935 | 45,800 | 1.9 | 136 |
| 40 | MCN-5 | BF28 | 20 | 16 | 184 | 2,834 | 8.0 | 75,045 | 32,093 | 2.3 | 105 |
| 41 | MCN-5 | BF28 | 20 | 21 | 180 | 2,098 | 5.1 | 78,727 | 34,126 | 2.3 | 115 |
| 42 | MCN-5 | BF28 | 40 | 7 | 205 | 7,221 | 13.6 | 63,430 | 27,141 | 2.3 | 72 |
| 43 | MCN-5 | BF28 | 40 | 9 | 180 | 5,009 | 13.4 | 66,660 | 32,076 | 2.1 | 74 |
| 44 | MCN-6 | BF28 | 10 | 32 | 155 | 1,177 | 3.0 | 36,925 | 17,570 | 2.1 | 126 |
| 45 | MCN-6 | BF28 | 10 | 34 | 147 | 1,050 | 3.6 | 36,661 | 16,238 | 2.3 | 131 |
| 46 | MCN-6 | BF28 | 20 | 24 | 181 | 1,839 | 5.4 | 41,070 | 17,875 | 2.3 | 110 |
| 47 | MCN-6 | BF28 | 20 | 29 | 157 | 1,311 | 3.4 | 39,952 | 18,405 | 2.2 | 129 |
| 48 | MCN-6 | BF28 | 40 | 12 | 197 | 4,076 | 10.4 | 39,677 | 17,016 | 2.3 | 78 |
| 49 | MCN-6 | BF28 | 40 | 16 | 175 | 2,635 | 9.0 | 37,787 | 17,897 | 2.1 | 83 |
| 50 | MCN-7 | BF28 | 10 | 35 | 162 | 1,126 | 3.1 | 96,574 | 43,762 | 2.2 | 126 |
| 51 | MCN-7 | BF28 | 10 | 40 | 147 | 890 | 7.3 | 97,660 | 49,981 | 2.0 | 131 |
| 52 | MCN-7 | BF28 | 20 | 22 | 160 | 1,724 | 6.2 | 75,482 | 41,502 | 1.8 | 108 |
| 53 | MCN-7 | BF28 | 20 | 31 | 170 | 1,301 | 5.2 | 99,796 | 52,561 | 1.9 | 120 |
| 54 | MCN-7 | BF28 | 40 | 17 | 199 | 2,900 | 12.5 | 66,070 | 38,185 | 1.7 | 76 |
| 55 | MCN-7 | BF28 | 40 | 16 | 200 | 3,091 | 13.7 | 57,150 | 31,239 | 1.8 | 71 |
| 56 | MCN-8 | BF20 | 5 | 19 | 164 | 2,090 | 2.6 | 54,255 | 16,315 | 3.3 | 140 |
| 57 | MCN-8 | BF20 | 10 | 24 | 166 | 1,669 | 3.2 | 60,477 | 25,551 | 2.4 | 133 |
| 58 | MCN-8 | BF20 | 20 | 14 | 204 | 3,543 | 7.6 | 48,686 | 12,539 | 3.9 | 110 |
| 59 | MCN-8 | BF20 | 30 | 14 | 183 | 3,093 | 12.2 | 63,987 | 21,056 | 3.0 | 96 |
| 60 | MCN-8 | BF20 | 40 | 12 | 203 | 4,100 | 8.4 | 60,951 | 23,170 | 2.6 | 82 |
| 61 | MCN-8 | BF28 | 0 | 13 | 137 | 2,573 | 0.0 | 69,479 | 26,481 | 2.6 | 153 |
| 62 | MCN-8 | BF28 | 5 | 17 | 192 | 2,788 | 3.1 | 68,198 | 22,954 | 3.0 | 145 |
| 63 | MCN-8 | BF28 | 20 | 14 | 210 | 3,633 | 8.4 | 74,549 | 18,333 | 4.1 | 111 |
| 64 | MCN-8 | BF28 | 30 | 9 | 178 | 4,921 | 9.2 | 71,186 | 27,270 | 2.6 | 98 |
| 65 | MCN-8 | BF28 | 40 | 10 | 222 | 5,619 | 11.6 | 87,234 | 22,403 | 3.9 | 79 |

General conditions: propylene = 160 psi; metallocene = 15 nmol; activator = 16.5 nmol; solvent = hexanes; total volume = 5 mL; tri(n-octyl)aluminum = 500 nmol.
Abbreviations: MCN is metallocene, act is activator, $C_2$ is ethylene, t is time, A is catalyst activity, Mw is weight average molecular weight, Mn is number average molecular weight, PDI is polydispersity defined as Mw/Mn, and Tm is melting point.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

The invention claimed is:

1. A process to polymerize propylene comprising contacting, at a temperature of 80° C. or more, propylene and optional comonomer with a homogeneous catalyst system comprising non-coordinating anion activator and one or more asymmetric metallocene catalyst compounds represented by the formula:

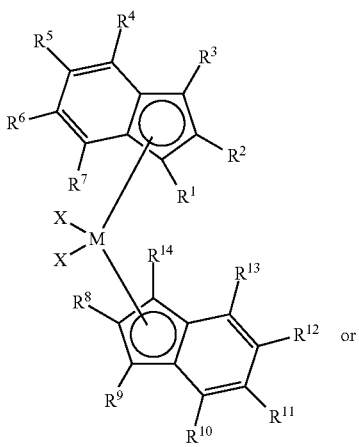

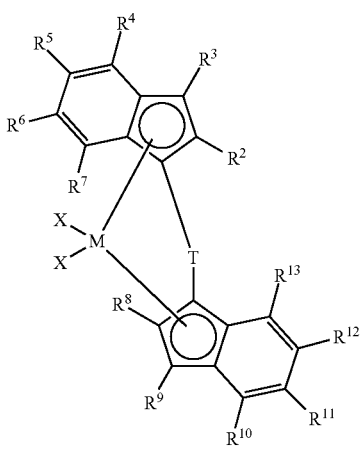

$R^2$ and $R^8$ are, independently, a $C_1$ to $C_{20}$ linear alkyl group where $R^8$ has at least 4 carbon atoms;

$R^4$ and $R^{10}$ are substituted or unsubstituted aryl groups, provided that at least one of the aryl groups is: 1) substituted at an ortho-position with at least one group selected from $C_1$ to $C_{40}$ hydrocarbyls, heteroatoms, and heteroatom containing groups and/or 2) substituted at the 3', 4' or 5'-position with at least one group selected from $C_1$ to $C_{40}$ hydrocarbyls, heteroatoms, and heteroatom containing groups;

M is a group 3 or 4 transition metal;

T is a bridging group;

each X is an anionic leaving group;

each $R^1$, $R^3$, $R^5$, $R^6$, $R^7$, $R^9$, $R^{11}$, $R^{12}$, $R^{13}$, and $R^{14}$ is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents; and where if the commoner comprises ethylene, then the ethylene is present at a partial pressure of up to 6900 kPa.

2. The process of claim 1, wherein $R^2$ is methyl, ethyl, n-propyl, n-butyl, n-pentyl, n-hexyl, n-heptyl, n-octyl, n-nonyl or n-decyl.

3. The process of claim 1, wherein $R^8$ is n-butyl, n-pentyl, n-hexyl, n-heptyl, n-octyl, n-nonyl or n-decyl.

4. The process of claim 1, wherein at least one of $R^4$ and $R^{10}$ is a phenyl group substituted at the 3' and 5'-positions with $C_1$ to $C_{10}$ alkyl groups or aryl groups or combinations thereof.

5. The process of claim 1, wherein $R^4$ and $R^{10}$ are independently a phenyl group substituted at the 3' and 5'-positions with $C_1$ to $C_{10}$ alkyl groups or aryl groups or combinations thereof and, optionally, the 4'-position is substituted with a group selected from $(XR'_n)^-$, wherein X is a Group 14-17 heteroatom having an atomic weight of 13 to 79 and R' is one of a hydrogen atom, halogen atom, a $C_1$-$C_{10}$ alkyl group, or a $C_6$-$C_{10}$ aryl group and n is 0, 1, 2, or 3.

6. The process of claim 1, wherein M is Hf, Ti and/or Zr.

7. The process of claim 1, wherein at least one of $R^4$ and $R^{10}$ is a phenyl group substituted at the 2'-position with an alkyl or aryl group.

8. The process of claim 1, wherein one of $R^5$ and $R^6$ or $R^{11}$ and $R^{12}$ join together to form a ring structure.

9. The process of claim 1, wherein T is represented by the formula $R_2^a J$, where J is C, Si, or Ge, and each $R^a$ is, independently, hydrogen, halogen, $C_1$ to $C_{20}$ hydrocarbyl or a $C_1$ to $C_{20}$ substituted hydrocarbyl, and two $R^a$ can form a cyclic structure including aromatic, partially saturated, or saturated cyclic or fused ring system.

10. The process of claim 1, wherein T is $CH_2$, $CH_2CH_2$, $C(CH_3)_2$, $SiMe_2$, $SiPh_2$, $SiMePh$, $Si(CH_2)_3$, $Si(CH_2)_4$, $Si(Me_3SiPh)_2$, or $Si(CH_2)_5$.

11. The process of claim 1, wherein the metallocene catalyst compound is represented by one or more of the following formulas:

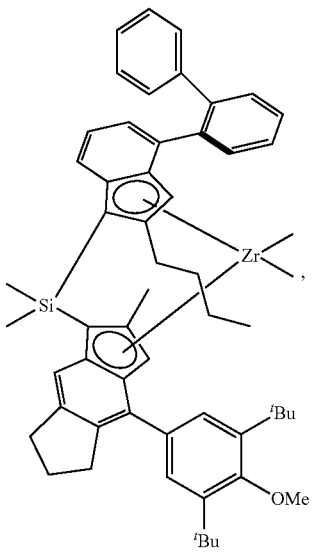

-continued

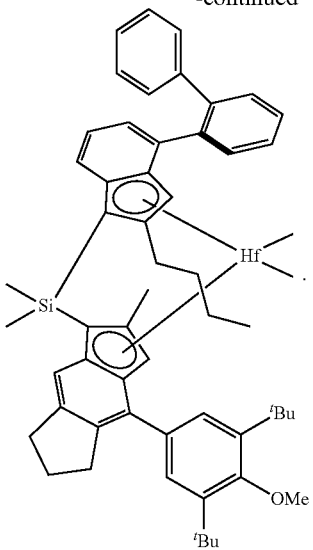

12. The process of claim 1, wherein when the metallocene catalyst compound comprises rac and meso isomers, the rac/meso ratio is 10:1 or greater.

13. The process of claim 1, wherein the activator comprises one or more anionic activators represented by the formula:

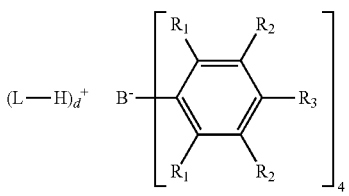

where:
each $R_1$ is, independently, a halide;
each $R_2$ is, independently, a halide, a $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group;
each $R_3$ is a halide, $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group;
wherein $R_2$ and $R_3$ can form one or more saturated or unsaturated, substituted or unsubstituted rings;
L is an neutral Lewis base; $(L-H)^+$ is a Bronsted acid; d is 1, 2, or 3;
wherein the anion has a molecular weight of greater than 1020 g/mol; and
wherein at least three of the substituents on the B atom each have a molecular volume of greater than 250 cubic Å.

14. The process of claim 1, wherein the activator comprises one or more of N,N-dimethylanilinium tetrakis(perfluoronaphthalen-2-yl)borate, N,N-dimethylanilinium tetrakis(perfluorobiphenyl)borate, N,N-dimethylanilinium tetrakis(perfluorophenyl)borate, N,N-dimethylanilinium tetrakis (3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, and triphenylcarbenium tetrakis(perfluorophenyl)borate.

15. The process of claim 1, wherein the activator comprises N,N-dimethylanilinium tetrakis(perfluoronaphthalen-2-yl)borate.

16. The process of claim 1, wherein the process occurs at a temperature of 90° C. or more.

17. The process of claim 1, wherein the process occurs at a temperature of from about 90° C. to about 200° C., at a pressure in the range of from about 0.35 MPa to about 10 MPa, and at a time up to 300 minutes.

18. The process of claim 1, wherein the polymerization occurs in the solution phase.

19. The process of claim 1, wherein $R^2$ and $R^8$ have no branches at the alpha or beta-positions.

20. The process of claim 1, wherein at least one of $R^2$ and $R^8$ has at least 6 carbon atoms.

21. The process of claim 1, wherein when the metallocene catalyst compound comprises rac and meso isomers, the rac/meso ratio is 30:1 or greater.

22. The process of claim 1 wherein when the metallocene catalyst compound comprises rac and meso isomers, the metallocene catalyst comprises greater than 55 mol % of the racemic isomer.

23. The process of claim 1 wherein when the metallocene catalyst compound comprises rac and meso isomers, the metallocene catalyst comprises greater than 85 mol % of the racemic isomer.

24. The process of claim 1, wherein $R^2$ is methyl and $R^8$ is n-butyl, n-pentyl, n-hexyl, n-heptyl, or n-octyl.

25. The process of claim 1, wherein the catalyst system is not supported on a support and is dissolved in the solvent/monomer mixture.

26. The process of claim 1 wherein $R^2$ is methyl and $R^8$ has at least 4 carbon atoms.

27. The process of claim 1 wherein $R^8$ has at least 6 carbon atoms.

28. The process of claim 1 wherein $R^4$ and $R^{10}$ are different.

29. The process of claim 1 wherein $R^2$ and $R^8$ are different.

30. The process of claim 1 wherein $R^4$ and $R^{10}$ are different and $R^2$ and $R^8$ are different.

31. The process of claim 1 wherein T is dialkylsilyl, $R^2$ is methyl, $R^8$ is butyl, and $R^5$ and $R^6$ are joined to form a non-aromatic ring containing 5 or 6 or 7 atoms.

32. The process of claim 1 wherein, M is zirconium, T is dialkylsilyl, $R^2$ is methyl, and $R^5$ and $R^6$ are joined to form a ring containing 5 or 6 or 7 atoms.

33. The process of claim 1 wherein T is dialkylsilyl, $R^2$ is methyl, $R^8$ is an unbranched alkyl group containing 2 to 14 carbons, and $R^5$ and $R^6$ are joined to form a ring containing 5 or 6 or 7 atoms.

34. The process of claim 1 wherein M is zirconium, T is dialkylsilyl, $R^2$ is methyl, $R^8$ is an unbranched alkyl group containing 2 to 14 carbons, and $R^5$ and $R^6$ are joined to form a ring containing 5 or 6 or 7 atoms.

35. The process of claim 1, wherein M is Zr.

36. The process of claim 1, wherein $R^2$ is methyl, $R^8$ is a C4-C20 linear alkyl, and $R^5$ and $R^6$ are hydrocarbyl.

* * * * *